(12) United States Patent
Lu et al.

(10) Patent No.: US 10,646,155 B2
(45) Date of Patent: May 12, 2020

(54) METHOD OF GENERATING AN ADAPTIVE PARTIAL REPORT AND APPARATUS FOR IMPLEMENTING THE SAME

(71) Applicants: OHIO STATE INNOVATION FOUNDATION, Columbus, OH (US); ADAPTIVE SENSORY TECHNOLOGY, Boston, MA (US)

(72) Inventors: Zhong-Lin Lu, Dublin, OH (US); Jongsoo Baek, Incheon (KR); Luis A. Lesmes, San Diego, CA (US)

(73) Assignees: OHIO STATE INNOVATIVE FOUNDATION, Columbus, OH (US); ADAPTIVE SENSORY TECHNOLOGY, Boston, MA (US)

( * ) Notice: Subject to any disclaimer, the term of this patent is extended or adjusted under 35 U.S.C. 154(b) by 256 days.

(21) Appl. No.: 15/567,028

(22) PCT Filed: Apr. 14, 2015

(86) PCT No.: PCT/US2015/025640
§ 371 (c)(1),
(2) Date: Oct. 16, 2017

(87) PCT Pub. No.: WO2016/167741
PCT Pub. Date: Oct. 20, 2016

(65) Prior Publication Data
US 2018/0098724 A1    Apr. 12, 2018

(51) Int. Cl.
*A61B 5/00*     (2006.01)
*G16H 15/00*    (2018.01)
(Continued)

(52) U.S. Cl.
CPC ............ *A61B 5/4064* (2013.01); *A61B 5/162* (2013.01); *A61B 5/4088* (2013.01);
(Continued)

(58) Field of Classification Search
CPC ................... A61B 5/40; A61B 5/4005; A61B 5/4029–4094; A61B 3/0033;
(Continued)

(56) References Cited

U.S. PATENT DOCUMENTS 6,832,069 B2 *  12/2004  Stout ..................... G09B 23/02
                                                           434/353
2003/0129574 A1  7/2003  Ferriol et al.
(Continued)

FOREIGN PATENT DOCUMENTS

WO    WO 2013/170091 A1    11/2013

OTHER PUBLICATIONS

Alcalá-Quintana et al., "Stopping rules in Bayesian adaptive threshold estimation," Spatial Vision, 2005, 18(3):347-74.
(Continued)

*Primary Examiner* — Eric F Winakur
*Assistant Examiner* — Chu Chuan Liu
(74) *Attorney, Agent, or Firm* — Michael Best & Friedrich LLP

(57) ABSTRACT

The invention provides a method of generating an adaptive partial report for an observer with an apparatus comprising a display, a user interface, and a processor. The apparatus can be a computer system or an electronic device, for example. The method includes the processor characterizing an iconic memory decay function for the observer. The characterization includes determining a prior for a plurality of parameters. The method further includes the processor determining a first stimulus for a first trial based on the prior for the plurality of parameters, the display generating the stimulus for viewing by the observer, the user interface receiving input for the first trial and in response to the stimulus, the processor revising respective parameter values for the parameters based on the received input, and the
(Continued)

processor determining a new stimulus for a next trial based on the revised parameter values.

20 Claims, 16 Drawing Sheets

(51) Int. Cl.
  *A61B 5/16* (2006.01)
  *G06F 3/041* (2006.01)
  *G06F 17/18* (2006.01)
  *G16H 50/20* (2018.01)
(52) U.S. Cl.
  CPC ............ *A61B 5/7264* (2013.01); *A61B 5/742* (2013.01); *A61B 5/7475* (2013.01); *G06F 3/041* (2013.01); *G06F 17/18* (2013.01); *G16H 15/00* (2018.01); *G16H 50/20* (2018.01)
(58) Field of Classification Search
  CPC ..... A61B 3/0041; A61B 3/005; A61B 3/0058; A61B 3/0091; A61B 3/032; A61B 3/06; A61B 3/063
  See application file for complete search history.

(56) References Cited

U.S. PATENT DOCUMENTS

| | | |
|---|---|---|
| 2011/0159467 A1 | 6/2011 | Peot et al. |
| 2012/0310299 A1 | 12/2012 | Kaula et al. |
| 2013/0204881 A1 | 8/2013 | Su |

OTHER PUBLICATIONS

Androutsopoulos et al., "Learning to Filter Spam E-Mail: A Comparison of a Naive Bayesian and a Memory-Based Approach," Machine Learning and Textual Information Access, 4th European Conference on Principles and Practice of Knowledge Discovery in Databases, 2000.
Atkinson et al., "Human memory: A proposed system and its control processes," Psychology of Learning and Motivation, vol. 2, 1968, pp. 89-195.
Baddeley et al., "Psychology of Learning and Motivation," Working Memory, 1974, vol. 8, pp. 47-89.
Becker et al., "The role of iconic memory in change-detection tasks," Perception, 2000, 29(3):273-86.
Berry et al., Bayesian Adaptive Methods for Clinical Trials. 2010, CRC Press.
Brainard, "The Psychophysics Toolbox," Spatial Vision, 1997, 10(4):433-436.
Cavagnaro et al., "Adaptive design optimization: a mutual information-based approach to model discrimination in cognitive science," Neural Computation, 2010, 22(4):887-905.
Chong et al., "Preclinical Alzheimer's disease: diagnosis and prediction of progression," Lancet Neurology, 2005, 4(9):576-9.
Cobo-Lewis, "An adaptive method for estimating multiple parameters of a psychometric function," Journal of Mathematical Psychology, 1996, 40, 353-354.
Cobo-Lewis, "An adaptive psychophysical method for subject classification," Perception & Psychophysics, 1997, 59(7):989-1003.
Coltheart, "Iconic memory and visible persistence," Perception & Psychophysics, 1980, 27(3):183-228.
Cowan, "The magical number 4 in short-term memory: A reconsideration of mental storage capacity," Behavioral and Brain Sciences, 2001, 24(1):87-114.
Dawid, "Bayes' Theorem and Weighing Evidence by Juries," Bayes's Theorem, 2005, pp. 70-90.
Di Lollo, "Temporal integration in visual memory," Journal of Experimental Psychology: General, 1980, 109(1):75-97.
Dick, "Iconic memory and its relation to perceptual processing and other memory mechanisms," Perception & Psychophysics, 1974, 16(3), 575-596.
Dixon et al., "Neurocognitive markers of cognitive impairment: exploring the roles of speed and inconsistency," Neuropsychology, 2007, 21(3), 381-99.
Dorr et al., "Rapid and Reliable Assessment of the Contrast Sensitivity Function on an iPad," Investigative Ophthalmology & Visual Science, 2013, 54(12):7266-73.
Dosher et al., "Mechanisms of perceptual learning," Vision Research, 1999, 39(19):3197-221.
Dowd, "Bayesian statistical data assimilation for ecosystem models using Markov Chain Monte Carlo," Journal of Marine Systems 68, 2007:439-456.
Edwards et al., "Bayesian statistical inference for psychological research," Psychological Review, 1963, 70(3):193-242.
Engle, "Working Memory Capacity as Executive Attention," Current Directions in Psychological Science, 2002, 11(1):19-23.
Fagan et al., "Inverse relation between in vivo amyloid imaging load and cerebrospinal fluid Abeta42 in humans," Annals of Neurology, 2006, 59(3):512-9.
Gegenfurtner et al., "Information transfer in iconic memory experiments," Journal of Experimental Psychology: Human Perception and Performance, 1993, 19(4):845-866.
Gu et al., "Bayesian Adaptive Estimation of Psychometric Slope and Threshold with Differential Evolution Not All Designs are Equally Informative," M. Knauff, Pauen M., Sebanz N., & I. Wachsmuth (Editors.), Proceedings of the 35th Annual Meeting of the Cognitive Science Society, Austin, TX: Cognitive Science Society. 2013, pp. 2452-2457.
Hebert et al., "Alzheimer disease in the United States (2010-2050) estimated using the 2010 census," Neurology, 2013, 80(19):1778-83.
Hou et al., "qCSF in clinical application: efficient characterization and classification of contrast sensitivity functions in amblyopia," Investigative ophthalmology & visual science, 2010, 51, 5365-5377.
James, The principles of psychology, vol. I, 1980, New York Holt.
Johnson, "Amyloid imaging of Alzheimer's disease using Pittsburgh Compound B," Current Neurology and Neuroscience Reports, 2006, 6(6):496-503.
Jonides et al., "Integrating visual information from successive fixations," Science, 1982, 215(4529):192-194.
Kim et al., "A Hierarchical Adaptive Approach to Optimal Experimental Design," Neural Comput., 2014, 26(11):2465-2492.
King-Smith et al., "Efficient and unbiased modifications of the QUEST threshold method: theory, simulations, experimental evaluation and practical implementation," Vision Research, 1994, 34(7):885-912.
Kontsevich et al., "Bayesian adaptive estimation of psychometric slope and threshold," Vision Research, 1999, 39(16), 2729-2737.
Kruschke, Doing Bayesian data analysis : a tutorial with R and BUGS. 2011. Burlington, MA: Academic Press.
Kujala et al., "A Bayesian-optimal principle for learner-friendly adaptation in learning games," Journal of Mathematical Psychology, 2010, 54(2), 247-255.
Kujala et al., "Bayesian adaptive estimation: The next dimension," Journal of Mathematical Psychology, 2006, 50(4), 369-389.
Leek, "Adaptive procedures in psychophysical research," Perception & Psychophysics, 2001, 63(8):1279-92.
Lesmes et al., "An adaptive method for estimating criterion sensitivity (d') levels in yes/no tasks," Journal of Vision, 2010, 6(6):1097-1097.
Lesmes et al., "Bayesian adaptive estimation of the contrast sensitivity function: the quick CSF method," Journal of vision, 2010, 10(3):17.1-21.
Lesmes et al., "Bayesian adaptive estimation of threshold versus contrast external noise functions: the quick TvC method," Vision Research, 2006, 46(19):3160-76.
Long, "Iconic memory: a review and critique of the study of short-term visual storage," Psychological Bulletin, 1980, 88(3):785-820.

(56) References Cited

OTHER PUBLICATIONS

Lu et al., "Characterizing observers using external noise and observer models: assessing internal representations with external noise," Psychological Review, 2008, 115(1):44-82.
Lu et al., "External noise distinguishes attention mechanisms," Vision Research, 1998, 38(9):1183-98.
Lu et al., "Fast decay of iconic memory in observers with mild cognitive impairments," Proceedings of the National Academy of Sciences of the United States of America, 2005, 102(5), 1797-802.
Lu et al., Visual Psychophysics: From Laboratory to Theory, 2013, pp. 385-418, The MIT Press.
Luck et al., "The capacity of visual working memory for features and conjunctions," Nature, 1997, 390(6657), 279-81.
Mintun et al., "[11C]PIB in a nondemented population: potential antecedent marker of Alzheimer disease," Neurology, 2006, 67(3), 446-52.
Myung et al., "Optimal experimental design for model discrimination," Psychological Review, 2009, 116(3):499-518.
Neisser, Cognitive psychology, 1967.
Pelli, "The VideoToolbox software for visual psychophysics: transforming numbers into movies," Spatial Vision, 1997, 10(4), 437-442.
Peripheral and Central Nervous System Drugs Advisory Committee. (2001). Vascular Dementia (vol. 66, pp. 75-76). U.S. Food and Drug Administration, Gaithersburg, MD.
Rentz et al., "Promising developments in neuropsychological approaches for the detection of preclinical Alzheimer's disease: a selective review," Alzheimer's Research & Therapy, 2013, 5(6), 58.
Rowe et al., "Amyloid imaging results from the Australian Imaging, Biomarkers and Lifestyle (AIBL) study of aging," Neurobiology of Aging, 2010, 31(8):1275-83.
Rowe et al., "Imaging beta-amyloid burden in aging and dementia," Neurology, 2007, 68(20):1718-25.
Shannon, "A mathematical theory of communication," Bell System Technical Journal, 1948, 27(3):379-423.
Sperling et al., "Toward defining the preclinical stages of Alzheimer's disease: recommendations from the National Institute on Aging-Alzheimer's Association workgroups on diagnostic guidelines for Alzheimer's disease," Alzheimer's & Dementia : The Journal of the Alzheimer's Association, 2011, 7(3), 280-92.
Sperling, "A Model for Visual Memory Tasks," Human Factors, 1963, vol. 5, issue 1, pp. 19-31.
Sperling, "Successive approximations to a model for short term memory," Acta Psychologica, 1967, 27, 285-92.
Sperling, "The information available in brief visual presentations," Psychological Monographs: General and Applied, 1960, 74(11):1-29.
Tanner, "Generalized adaptive procedure for psychometric measurement," Perception, 37(ECVP Abstract Supplement), 93 (2008).
Treutwein, "Adaptive psychophysical procedures," Vision Research, 1995, 35(17):2503-22.
Watson et al., "QUEST: a Bayesian adaptive psychometric method," Perception & Psychophysics, 1983, 33(2):113-120.
Wimo et al., "Health Economics of Severe Dementia," Severe Dementia, 2006, Chapater 19, pp. 227-236.
Yang et al., "Bayesian phylogenetic inference using DNA sequences: a Markov Chain Monte Carlo Method," Molecular Biology and Evolution, 1997, 14(7):717-24.
Yang, "Lifetime of Human Visual Sensory Memory: Properties and Neural Substrate," Dissertation submitted to the University of Pennsylvania, 1999, 142 pages.
International Search Report and Written Opinion for Application No. PCT/US2015/025640 dated Jan. 29, 2016 (19 pages).

\* cited by examiner

Table 1: *Parameters of three simulated observers*

|        | Observer 1 | Observer 2 | Observer 3 |
|--------|------------|------------|------------|
| $a_0$  | .35        | .25        | .25        |
| $a_1$  | .95        | .85        | .85        |
| τ(sec) | .40        | .40        | .10        |

Table 2: *Accuracy and Precision of qPR Simulations. Average widths of 67% credible intervals are given in parentheses (units: percent correct).*

|            | Observer 1 | Observer 2 | Observer 3 |
|------------|------------|------------|------------|
| 20 trials  | -2.6%      | .8%        | 7.4%       |
|            | (9.6%)     | (10.3%)    | (11.1%)    |
| 50 trials  | .1%        | 1.7%       | 3.9%       |
|            | (7.2%)     | (8.0%)     | (8.8%)     |
| 100 trials | .9%        | 1.7%       | 2.0%       |
|            | (5.7%)     | (6.3%)     | (6.8%)     |
| 200 trials | .7%        | 1.1%       | 1.0%       |
|            | (4.3%)     | (4.7%)     | (4.9%)     |

*Fig. 9*

Table 3: Number of trials required to reach a 7.5% precision.

|       | Observer 1 | Observer 2 | Observer 3 |
|-------|------------|------------|------------|
| MCS   | 240        | 272        | 272        |
| qPR   | 44         | 64         | 78         |
| Ratio | 5.45       | 4.25       | 3.49       |

Number of trials required to reach a 5% precision

|       | Observer 1 | Observer 2 | Observer 3 |
|-------|------------|------------|------------|
| MCS   | 536        | 616        | 608        |
| qPR   | 142        | 174        | 189        |
| Ratio | 3.77       | 3.54       | 3.22       |

*Fig. 10*

Table 4: *Accuracy and precision of qPR in the psychophysical experiment (units: percent correct)*

|  | RMSE | Precision | Test-Retest (Coefficient) |
|---|---|---|---|
| 20 trials | 11.1% | 9.5% | .7814 |
| 50 trials | 7.4% | 6.8% | .8920 |
| 100 trials | 6.3% | 5.1% | .9301 |
| 200 trials | 4.9% | 3.9% | .9582 |

METHOD OF GENERATING AN ADAPTIVE PARTIAL REPORT AND APPARATUS FOR IMPLEMENTING THE SAME

CROSS-REFERENCE TO RELATED APPLICATION(S)

This application is a U.S. national stage entry of International Patent Application No. PCT/US2015/025640, filed on Apr. 14, 2015, the entire contents of which are fully incorporated herein by reference.

BACKGROUND

The invention relates to an adaptive testing method of generating a partial report such as for iconic memory. The invention also relates to an apparatus, such as an electronic device or computer system, for implementing the adaptive partial report procedure.

It has been known that human memory is composed of three sub-storages: sensory memory, short-term memory, and long-term memory. Sensory memory is the literal, modality-specific neural representation of sensory stimuli in the human brain. Sensory inputs from the environment are initially stored in sensory memory and processed in subsequent stages of perception and cognition. The existence of sensory memory was first demonstrated in the 1960s, in experiments in which three rows of letters were briefly displayed, and observers were asked to report the identity of the letters in one of the rows cued with a high, middle, or low frequency tone after a variable delay.

For example, FIG. 1a is an illustration of screen shots for a partial-report procedure. After a brief presentation of stimulus (a 3×4 array of letters) followed by a blank screen, the observer is given a sound cue. The observer is to report letters of the cued row in the partial report condition. Item recognition in the partial-report condition was compared with the whole-report condition, in which observers were asked to report all items from the display. FIG. 1b provides exemplary results of a partial report experiment. The performance difference between the partial report and whole report conditions is called the 'partial report superiority effect'. The effect demonstrates performance benefits from iconic memory. The number of the estimated available items in sensory memory decreases rapidly with increasing test delay in partial report and approaches the whole-report asymptote in about 200-300 ms.

During the past half-century, sensory memory has been extensively studied and has been widely accepted as a critical component in many theories on human information processing. Recently, one of the inventors of this application compared, as part of a study, iconic memory decay functions of young, old normal, and old observers with mild cognitive impairment (MCI). The study found that iconic memory decayed much faster in the MCI group than the others (FIG. 2). FIG. 2 is a graph representing a decay function of three groups of observers or subjects. Because more than 80% of people with MCI develop Alzheimer's disease in 10 years, this finding suggested that faster decay of iconic memory might be an early sign of Alzheimer's disease.

Conventionally, the method of constant stimuli (MCS) is used to measure the memory decay function. Subjects' (or observers') responses at a number of pre-selected cue delays are measured with about 100 trials per delay. An empirical memory decay function is obtained by estimating the number of available items in sensory memory at each delay from observers' responses. Often a theoretical curve such as an exponential decay function is fit to the empirical data to characterize the memory decay process. In a typical study, between 600 and 800 test trials (6-8 cue delays×100 trials/delay) are necessary to obtain a good estimate of the sensory memory decay function. It takes approximately one hour for normal young observers but much longer for observers in special populations. The long testing time makes it difficult or even impossible to carry out partial report experiments in special populations.

Many adaptive procedures have been developed to reduce the burden of data collection in psychophysical experiments. Most development has focused on characterizing psychometric functions, including various non-parametric procedures for estimating a single threshold, and Bayesian adaptive procedures for estimating either a single threshold or the threshold and slope of a psychometric function. Recent development in this area has extended adaptive procedures to measure various psychological functions, including the threshold versus contrast function, contrast sensitivity function, and sensitivity and bias parameters in Yes-No tasks. In all these adaptive procedures, the stimulus in the next trial is determined by the observer's previous responses to improve the efficiency of the test.

SUMMARY

The invention alleviates the testing demand in the partial report procedure by developing a new adaptive procedure for estimating sensory memory decay function with a small number of trials, without sacrificing its accuracy and precision.

In one embodiment, the invention provides a method of generating an adaptive partial report for an observer with an apparatus comprising a display, a user interface, and a processor. The method includes the processor characterizing an iconic memory decay function for the observer. The iconic memory decay function has a plurality of parameters. The characterization includes determining a prior for the plurality of parameters. The method further includes the processor determining a first stimulus for a first trial based on the prior of the parameters. The determined stimulus is expected to lead to an information gain for the estimated iconic memory decay function. The method also includes the display generating the stimulus for viewing by the observer, the user interface receiving input for the first trial and in response to the stimulus, the processor revising a posterior distribution of the parameters based on the received input, and the processor determining a new stimulus for a next trial based on the revised posterior distribution. The determined new stimulus is expected to lead to additional information gain for the estimated iconic memory decay function. The method can also include the display generating the new stimulus for viewing by the observer, the user interface receiving new input for the next trial and in response to the stimulus, and the processor revising the posterior distribution of the parameters based on the new input.

In another embodiment the invention provides an apparatus for generating an adaptive partial report, such as for iconic memory. The apparatus can be an electronic device or computer system. The apparatus includes a display, a user interface, a processor, and a non-transitory medium comprising instructions. The processor can execute the instructions to perform the method of generating the adaptive partial report for the observer.

Other aspects of the invention will become apparent by consideration of the detailed description and accompanying drawings.

BRIEF DESCRIPTION OF THE DRAWINGS

FIG. 9 is a table providing accuracy and precision of adaptive PR simulations

FIG. 10 is tables providing number of trials reach various precisions.

DETAILED DESCRIPTION

Figure 1A:
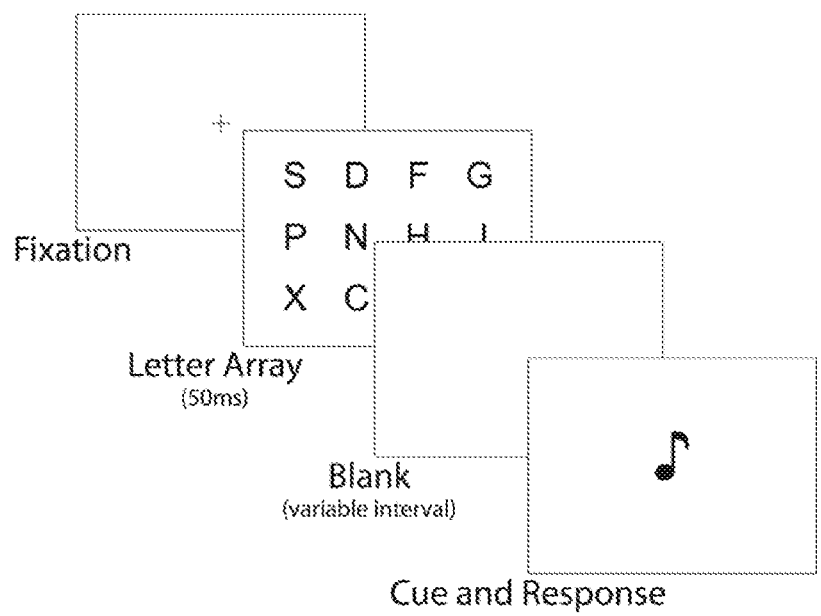
FIG. 1a is an illustration of screen shots for a partial-report procedure.
Figure 1B:
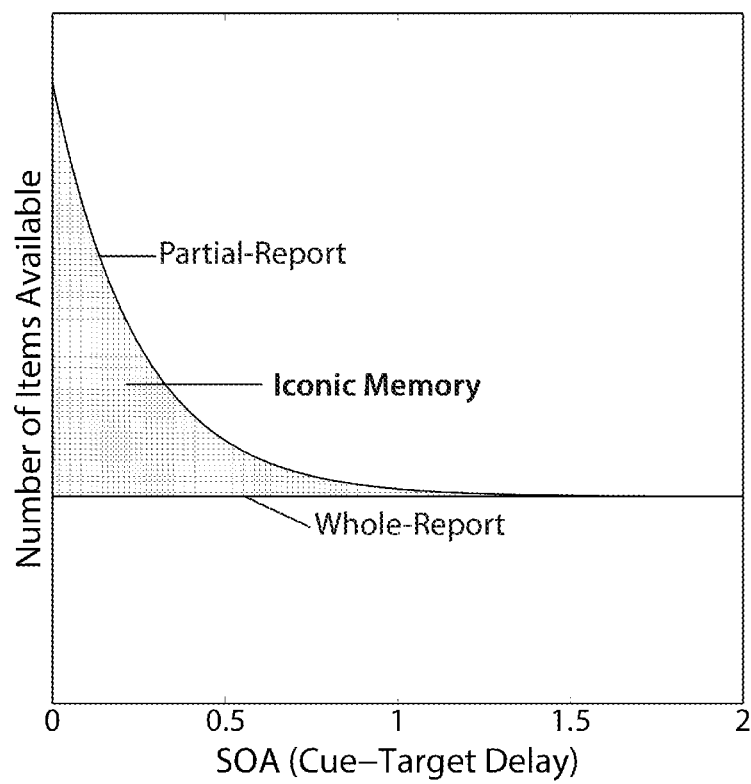
FIG. 1b is a graph providing exemplary results of a partial report experiment.
Figure 2:
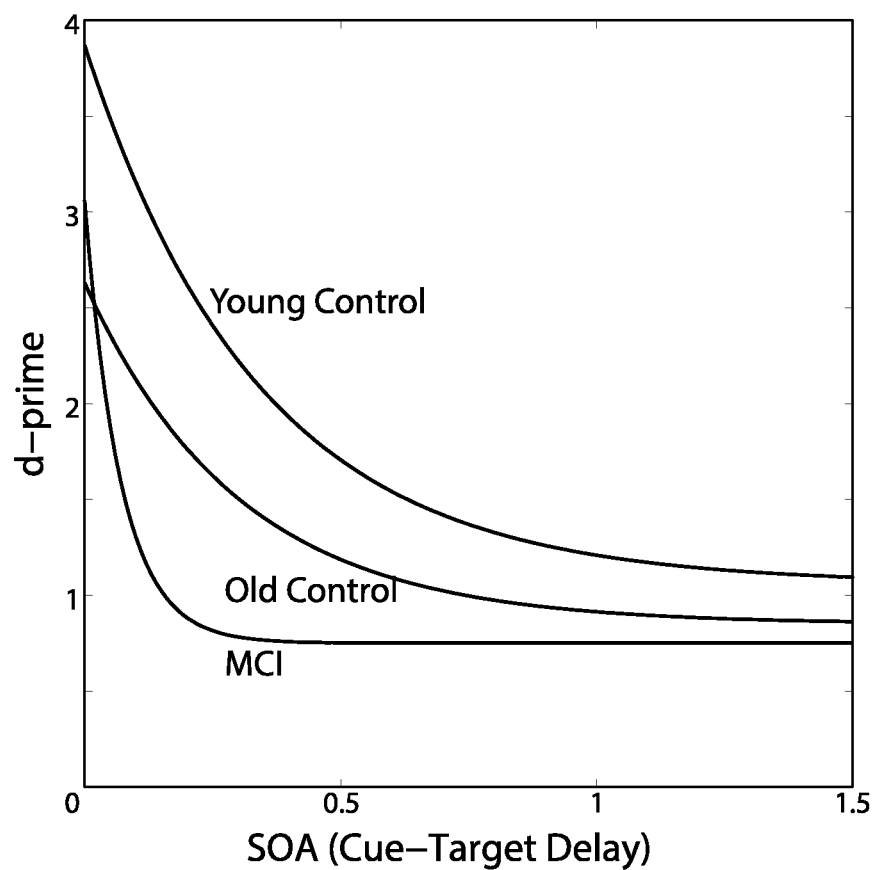
FIG. 2 is a graph representing a decay function of three groups of observers.

Before any implementations of the invention are explained in detail, it is to be understood that the invention is not limited in its application to the details of construction and the arrangement of components set forth in the following description or illustrated in the following drawings. The invention is capable of other implementations and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. The term "set" is used broadly to refer to one or more. Also, electronic communications and notifications may be performed using other known means including direct connections, wireless connections, etc.

It should also be noted that a plurality of hardware and software based devices, as well as a plurality of different structural components may be utilized to implement the invention. Furthermore, and as described in subsequent paragraphs, the specific configurations illustrated in the drawings are intended to exemplify implementations of the invention. Alternative configurations are possible.

An adaptive partial report (adaptive PR) method utilizing an adaptive partial report procedure includes four steps in one implementation. First, the iconic memory decay function is characterized with an exponential decay function with a broad prior distribution of the parameters. Second, the stimulus for the next trial is selected as the one that would lead to the most information gain on the estimated iconic memory decay function. Third, following observer's response, the posterior distribution of the parameters is updated using Bayes rule. Finally, the second and third steps are repeated until a fixed number of trials or a pre-set test precision is reached. The method substantially increases the efficiency of partial report experiments by exploiting the regularity of the iconic memory decay function, Bayesian update, and optimal stimulus selection.

Figure 3:
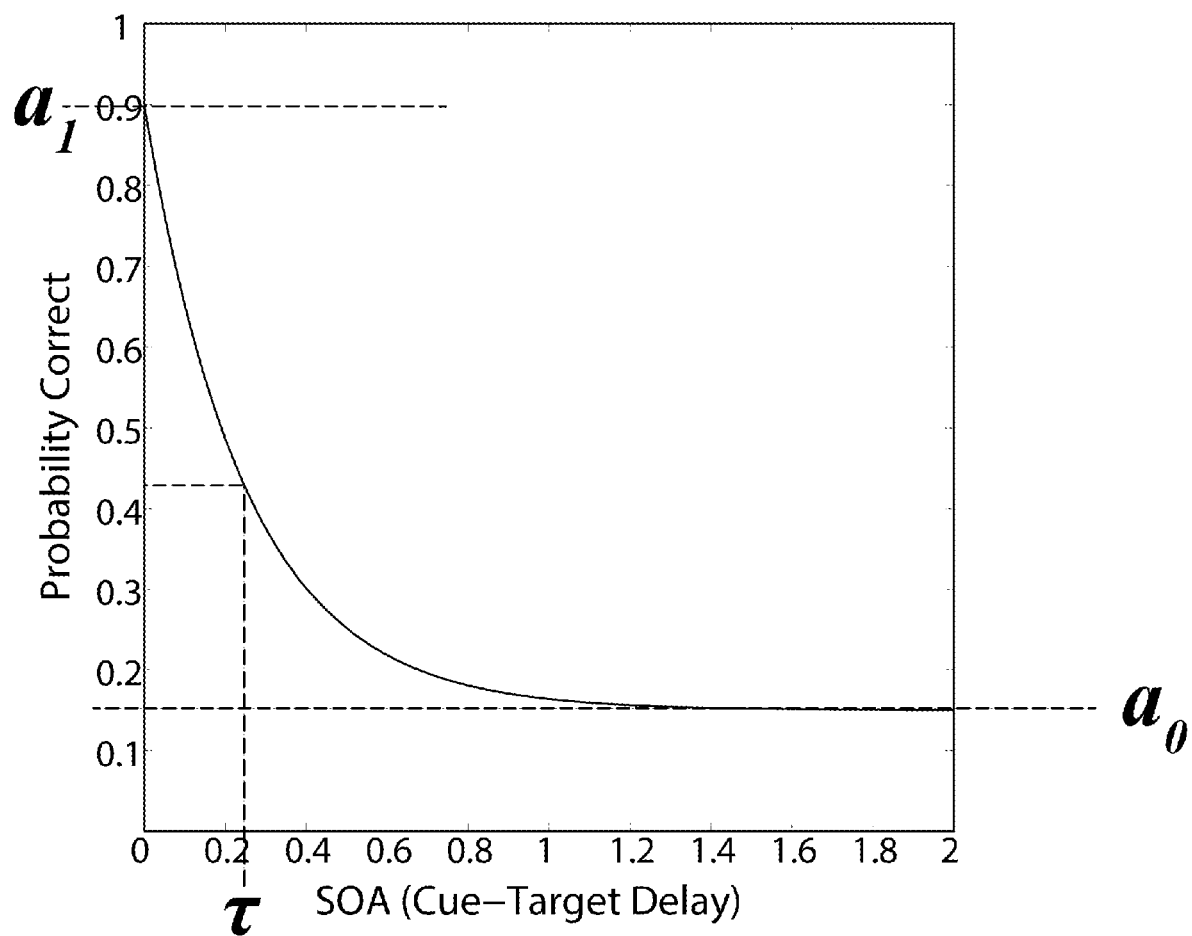
FIG. 3 is a graph representing parameterization of the iconic memory decay function.

With regard to parameterization, one sensory memory decay function that has been traditionally modeled is an exponential decay as shown in FIG. 3. Eq. 1 represents the formula of FIG. 3

$$pc(SOA) = a_0 + (a_1 - a_0)e^{-SOA/\tau} \quad \text{(eq. 1)}$$

where pc(SOA) is the probability of making a correct response at cue delay time SOA (target display and cue stimuli onset asynchrony), $a_0$ is the asymptotic performance level, often associated with residual information in short-term memory after iconic memory decays completely, $a_1$ is the performance level when SOA=0, and $\tau$ is the time constant of memory decay—the time it takes for human performance to drop to 37% of its initial level. Each set of parameter values $\vec{v} = [a_0, a_1, \tau]$ describes a complete memory decay function. The initial distributions of the parameters are described by a prior probability density function. One purpose in some embodiments of the adaptive PR procedure is to obtain accurate and precise estimates of the three parameters as efficiently as possible through trial-by-trial update of their posterior distribution.

In some implementations, the iconic memory decay function can be based on the sensitivity index or d', a statistic used in signal detection theory that provides the separation between the means of the signal and the noise distributions, compared against the standard deviation of the noise distribution. The functional form can assume a different formula (e.g., power function) that has a general decaying characteristic. The functional form can also incorporate subjective lapse, finger errors, etc.

For estimation through a Bayesian update, in some implementations of the invention, the adaptive PR procedure estimates the three parameters of the iconic memory decay function using Bayesian inference. That is, using Bayesian inference, the procedure starts with the prior probability distribution and updates the probability distribution of the parameters based on the observer's responses.

In some implementations, the prior distribution of the parameters and the sampling range and grid of the parameters can be informed by other characteristics of the observer (e.g., demographic information), and/or posterior distribution(s) of the same observer or other observers in previous study sessions.

In the beginning of one adaptive PR procedure, the prior probability distribution, $p_{t=0}(\vec{v})$, is defined as a three-dimensional joint probability distribution. The prior probability space represents all possible iconic memory decay functions. After the $t^{th}$ trial, the prior distribution, $p_t(\vec{v})$, can be updated to the posterior distribution, $p_t(\vec{v}|r_t)$, with the observer's response, $r_t$, by Bayes rule:

$$p_t(\vec{v}/r_t) = \frac{p(r_t/\vec{v})}{\sum [p_t(\vec{v}) \times p(r_t/\vec{v})]} \times p_t(\vec{v}) \quad \text{(eq. 2)}$$

The likelihood of observing a response (correct or incorrect) given the parameter set, $p_t(r_t|\vec{v})$, can be generated from the iconic memory decay function (Eq. 1). The posterior $p_t(\vec{v}|r_t)$ following trial t serves as the prior $p_{t+1}(\vec{v})$ for the next trial. The best estimate of the decay function can be the mean of resampled decay functions from the posterior distribution.

Next, for the stimulus selection, the process can use a one-step ahead search for minimum entropy. To select the stimulus for the next trial, the adaptive PR determines the SOA, from equation 1, that would maximize the expected information gain about the parameters of the iconic memory decay function. Here, information is quantified by entropy, a measure of uncertainty associated with variable. For example, the search first predicts observer's response to every possible SOA in the next trial based on the current estimated posterior. The process then computes the expected posterior distribution for each possible SOA. The SOA with the minimum expected entropy is chosen for the next trial. This is equivalent to maximizing the expected information gain, quantified as the entropy change between the prior and posterior.

The one-step-ahead search for expected entropy over multiple parameters may require intensive computations. Integration of modern computational algorithms, such as Markov-Chain Monte Carlo sampling, into adaptive PR reduces computation time and makes it possible to use the adaptive PR in real time experiments without delay between each computation. MCMC methods are a class of algorithms that are based on sampling or estimating the posterior distributions as a function of the multi-dimensional parameter and multi-dimensional stimulus spaces. It is estimated that MCMC algorithms may reduce the computational load by a factor of 100 or more.

In some implementations, instead of maximizing the expected information gain about the parameters of the iconic memory decay function, other utility functions that maximize other objective functions (e.g., only the decay parameter, change of iconic memory decay function due to disease progression or therapeutic response, or discrimination of different groups of subjects) can also be implemented. Alternative objective functions for optimization can also include minimizing the credible intervals of single partial report parameters, minimizing the credible regions of the estimated partial report functions, minimizing the uncertainty of class membership in patient discrimination, maximizing the probability gain for the hypothesis of class membership, and maximizing the expected change in Kullback-Leibler distance between the Bayesian prior and posterior.

In some implementations, the one-step-ahead search can be replaced with multiple-steps-ahead search algorithms that maximize information gain over multiple trials. The search can also incorporate considerations of other features of the test (e.g., total test time) in determining the optimal test sequence.

With regard to the stopping rule, in one implementation of the process, the adaptive PR is iterated for a fixed number of trials. Alternatively, the adaptive PR procedure can stop after it achieves a certain level of precision for defined objectives (e.g., all the parameters, credible interval of the decay function, or decay time constant).

Embodiments of the invention, described as an estimation procedure of iconic memory decay function, can also be implemented as a procedure to classify patients based on their performance and knowledge of different patient categories. In the case of discrimination, it is not the partial report parameters that are estimated, but the probability that the test subject is a member of a class defined by a prototypical partial report function that can signify normal or impaired memory.

Figure 4:
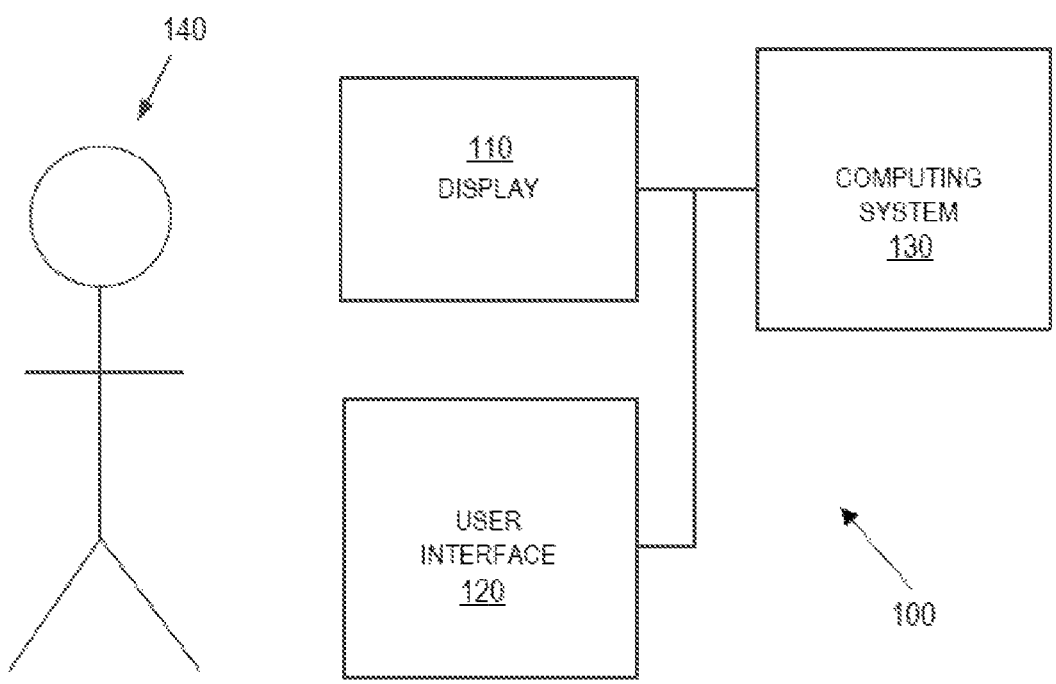
FIG. 4 is a block diagram illustrating components of a system for implementing adaptive PR procedure.

One exemplary system utilizing the invention is shown in FIG. 4. FIG. 4 represents a system 100 for implementing the adaptive PR procedure. The system 100 includes a display 110 coupled to a user interface 120 and a computing system 130. An observer (or subject, user, or patient) 140 can interact with the user interface 120 and/or display 110. The system can include, for example, a personal computer or a mobile device such as a smart phone or tablet computer and can have network connectivity for communication with other computing systems or servers. The user interface 120 can integrate with the display 110, for example, as a touch screen display. High quality visual stimuli, with accurate control of luminance/color, spatial pattern and layout, and display timing can be accommodated based on display resolution and size. A constant viewing distance is achieved through the use of a chinrest or other similar devices. The observer 120 can perform the adaptive PR procedure using the system by, for example, viewing a letter array image (such as one shown in FIG. 1A) on the display 110. In one implementation, the observer provides feedback to the interface 120, while the computing system 130 establishes the adaptive PR. The observer 140 can indicate or draw a response using the user interface 120. Identification can be done by key press of recognized letters, and/or the observer can verbally respond for recognition by verbal recognition software. It is also envisioned that the observer may provide feedback through the assistance of a clinician proctoring the observer. The computing system 130 can determine the one or more parameters from the result of the stimulus test and determine the one or more second parameters using the statistical inference. An example system 100 is an IBM PC compatible computer with a keyboard, running software for stimulus presentation, in addition to scientific computing software that implements the adaptive PR algorithm. The stimuli were displayed on a Dell 17-inch color CRT monitor, whose refresh rate was set at 100 Hz. Matlab programs can be written with Psychtoolbox extensions to be used to present visual stimuli; the computer keyboard is used to collect observer responses; and the adaptive PR algorithm is used to select stimulus conditions and estimate the sensory memory decay function.

Figure 5:
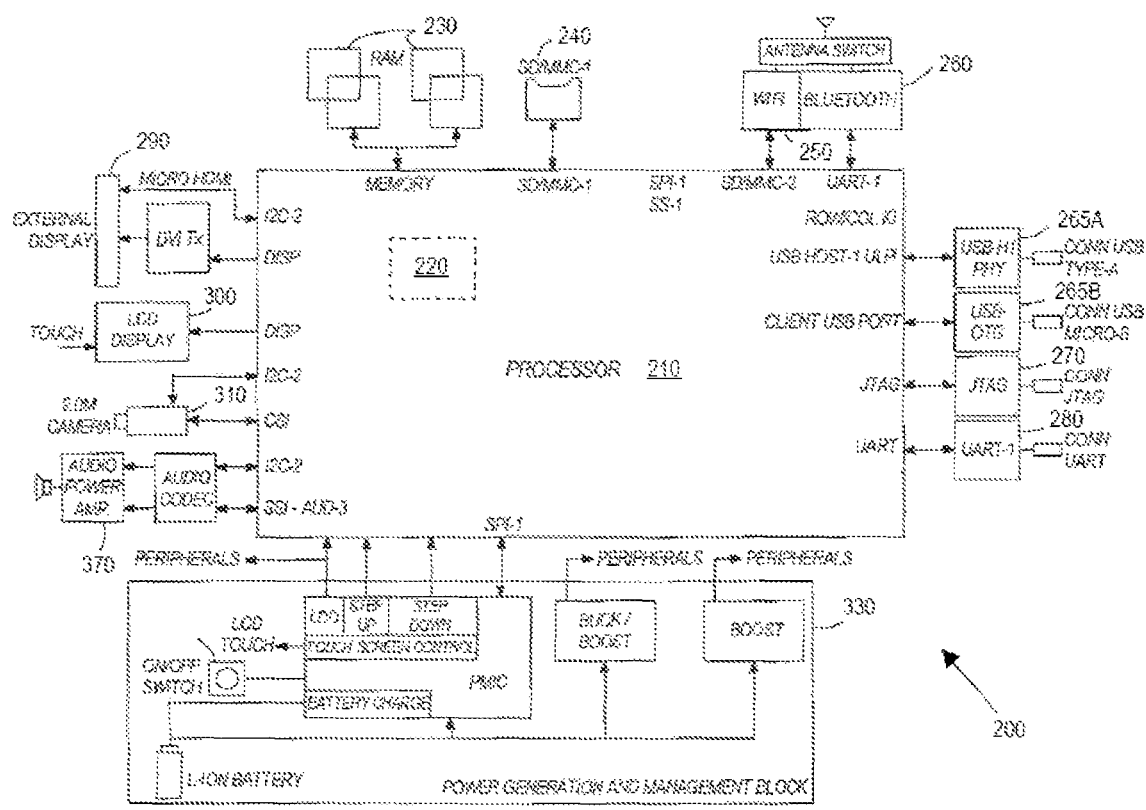
FIG. 5 is a block diagram illustrating a device for implementing adaptive PR procedure.

Alternatively, the system can take the form of a single device. FIG. 5 shows a block diagram of one construction of the device 200. The device 200 includes a printed circuit board ("PCB") that is populated with a plurality of electrical and electronic components that provide power, operational control, and protection to the device 200. With reference to FIG. 5, the device 200 includes a processor 210. The processor 210 is a controller for controlling the device 200. In one construction, the processor 210 is an applications processor. More specifically, the applications processor has internal instruction and data caches, multimedia capabilities, external memory interfacing, and interfacing flexibility. Of course, other processing units, such as other microprocessors, microcontrollers, digital signal processors, etc., can be used in place of the processor 210.

The device 200 includes memory, which can be internal to the processor 210 (e.g., memory 220), external to the processor 200 (e.g., RAM 230), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 210 executes software that is capable of being stored in the RAM (e.g., during execution), the ROM (e.g., on a generally permanent basis), or another non-transitory computer readable medium such as another memory or a disc. The device 200 also includes input/output ("I/O") systems that include routines for transferring information between components within the processor 210 and other components of the device 200 or external to the device 200.

Software included in the implementation of the device 200 is stored in the memory 220 of the processor 210, RAM 230, ROM, or external to the device 200. The software includes, for example, firmware, one or more applications, program data, one or more program modules, and other executable instructions. The processor 210 is configured to retrieve from memory and execute, among other things, instructions related to the control processes and methods described below for the device 200. For example, the processor 210 is configured to execute instructions retrieved from the memory 220, RAM 230, and/or ROM for providing an adaptive PR procedure.

One memory shown in FIG. 5 is RAM 230, which can be a double data rate (DDR2) synchronous dynamic random access memory (SDRAM) for storing data relating to and captured during the operation of the device 200. In addition, a secure digital (SD) or multimedia card (MMC) can be coupled to the device 200 for transferring data from the device 200 to the memory card via slot 240. Of course, other types of data storage devices can be used in place of the data storage devices shown in FIG. 5.

The device 200 can also include multiple bi-directional radio communication capabilities. Specific wireless portions that can be included with the device 200 are a WiFi bi-direction radio communication portion 250 and a Bluetooth bi-direction radio communication portion 260. The WiFi portion 250 and Bluetooth portion 260 include a WiFi communication interface, a Bluetooth communication interface, an antenna switch, and a related antenna all of which allows wireless communication following the WiFi Alliance standard and Bluetooth Special Interest Group standard. Of course, other wired, wireless local area network (WLAN) standards, and wireless personal area networks (WPAN) standards can be used with the device 200.

The device 200 can include multiple communication portions for wired communication. Exemplary circuitry and ports for receiving a wired connector include a portion and related port for supporting universal serial bus (USB) connectivity 265, including a Type-A port and a Micro-B port; a portion and related port for supporting Joint Test Action Group (JTAG) connectivity 270, and a portion and related port for supporting universal asynchronous receiver/transmitter (UART) connectivity 280. Of course, other wired communication standards and connectivity can be used with or in place of the types shown in FIG. 5.

Another device connectable to the device 200, and therefore supported by the device 200, is an external display. The connection to the external display can be made via a micro High-Definition Multimedia Interface (HDMI) 290, which provides a compact audio/video interface for transmitting uncompressed digital data to the external display. The use of the HDMI connection 290 allows the device 200 to transmit video (and audio) communication to an external display. Of course other connection schemes, such as DVI, can be used with the device 200.

The device 200 includes a touch screen I/O device 300 for providing a user interface with the clinician. The touch screen display 300 can be a liquid crystal display (LCD) having a resistive, capacitive, or similar touch-screen technology. It is envisioned that multitouch capabilities can be used with the touch screen display 300 depending on the type of technology used. Alternative means for providing input to the device 200 are envisioned, including wired and wireless input devices.

The device 200 includes a camera 310 allowing the device to take pictures or video. The resulting image files can be used to document a procedure or an aspect of the procedure, such as viewing distance. Similarly, the device 200 includes an audio portion 370 having an audio codec circuit, audio power amplifier, and related speaker for providing audio communication to the observer, such as the clinician or the patient.

The device 200 further includes a power generation and management block 330. The power block 330 has a power source (e.g., a lithium-ion battery) and a power supply for providing multiple power voltages to the processor, LCD touch screen, and peripherals.

The device 200 can be a handheld computing tablet with touch screen capabilities. The tablet is a portable personal computer with a touch screen, which is typically the primary input device. However, an external keyboard or mouse can be attached to the device 200. The tablet allows for mobile functionality not associated with even typical laptop personal computers, which can be used in some embodiments of the invention. It is also envisioned that the device 200 can be coupled with a remote server that implements aspects of the invention discussed herein. For example, various processes discussed herein may be performed interactively between the device 200 and the remote server and/or certain processes, such as setting the most appropriate prior for a given observer, can be performed at a later time after the procedure at the remote server.

To evaluate the performance of the adaptive PR procedure for observers with a range of partial report functions, the inventors simulated three observers with distinct parameter values that approximately corresponded to young, old normal, and old MCI groups from the article titled "Fast decay of iconic memory in observers with mild cognitive impairments", published in *Proceedings of the National Academy of Sciences of the United States of America*, 102(5), at pp. 1797-802. The parameters of the simulated observers are summarized in Table 1 of FIG. 6.

The parameter space was based on results of previous iconic memory studies, with $a_0$ from 0% to 50% (41 samples), $a_1$ from 50% to 100% (41 samples), and $\tau$ from 0.01 to 0.08 sec (40 samples) in linear space. The sufficiently broad parameter space enables robust assessments of various populations and avoids effects of extreme values—the tendency to bias toward the center of the parameter space when the observer's true parameter values are close to the boundary of the space. The priors were set to a uniform distribution.

Potential testing conditions are defined by different possible SOAs, which were sampled from 0 seconds to 3 seconds with 30 equally spaced samples on a logarithmic scale. The range was broader than what is commonly used in partial report studies (0-1.5 sec). Including test trials at long SOAs can allow improved estimates of the asymptotic level $a_0$ of the iconic memory decay function.

The inventors assumed that simulated observers were performing a 10-alternative forced-choice (10AFC) letter identification task in a partial report procedure, in which each letter can be any one of a set of 10 letters and observers must respond with one of the 10 letters in each trial. Each simulation consisted of 200 trials. In each trial, the expected percent correct, pc, of the simulated observer was calculated for the selected SOA. Observer's response in each trial was simulated by sampling a random number r from a uniform distribution. The response was labeled as correct if r<pc, and incorrect otherwise. Simulation of each observer was repeated 1000 times.

Accuracy is a measure of how much the adaptive PR estimates deviate from the true iconic memory decay function on average, and precision is a measure of the variability of the adaptive PR estimates. A good procedure should rapidly increase the accuracy of the estimated decay function as trial number increases and lead to an unbiased estimate. Bias can be calculated by the mean discrepancy between the estimated and true iconic memory decay function. The bias of estimated decay functions at t-th trial can be calculated with Equation 3:

$$bias_i = \frac{\sum_k \sum_j (pc_{ijk}^{sim} - pc_k^{true})}{J \times K} \quad \text{(eq. 3)}$$

where $pc_{ijk}^{sim}$ is the estimated probability correct of k-th SOA obtained in the j-th simulation and $pc_k^{true}$ is the true probability correct we simulated.

Figures 6, 7:
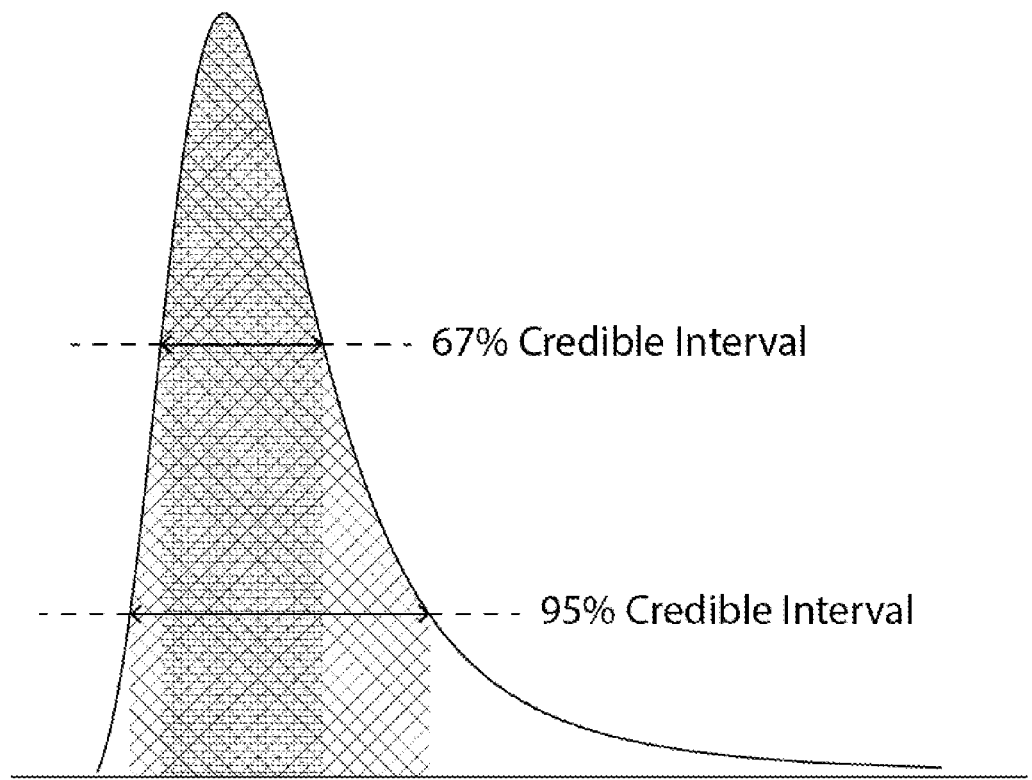
FIG. 6 is a table providing parameters of three simulated observers
FIG. 7 is a graph representing a Bayesian credible interval.

Precision is defined as the inverse of the variability of the estimates. As a measurement of precision, one can compute the half width of the average credible interval of the posterior distribution of the estimated iconic memory decay function. The credible interval refers to the shortest interval that covers most of the distribution (see FIG. 7 for an example). 95% credible interval represents a 95% probability that the actual value lies within the range, whereas confidence interval, the most popular indices of precision, represents an interval that contains the true value of the parameter for 95% of unlimited repetitions. Since researchers typically do not iterate an experiment many times for the same observer, the credible interval of posterior distribution is a good index of performance that can be obtained with a single run of the experiment. FIG. 7 represents a Bayesian credible interval. Shaded regions with dark-gray and light-gray represent 67% and 95% credible intervals of the probability distribution. A credible interval represents the shortest interval that covers a particular percentage (e.g. 67% or 95%) of total area. In contrast to confidence interval, the lower and upper bounds always have the same probability densities and the probability densities within the credible interval are greater than those outside of the interval, in even asymmetric distributions.

Figure 8:
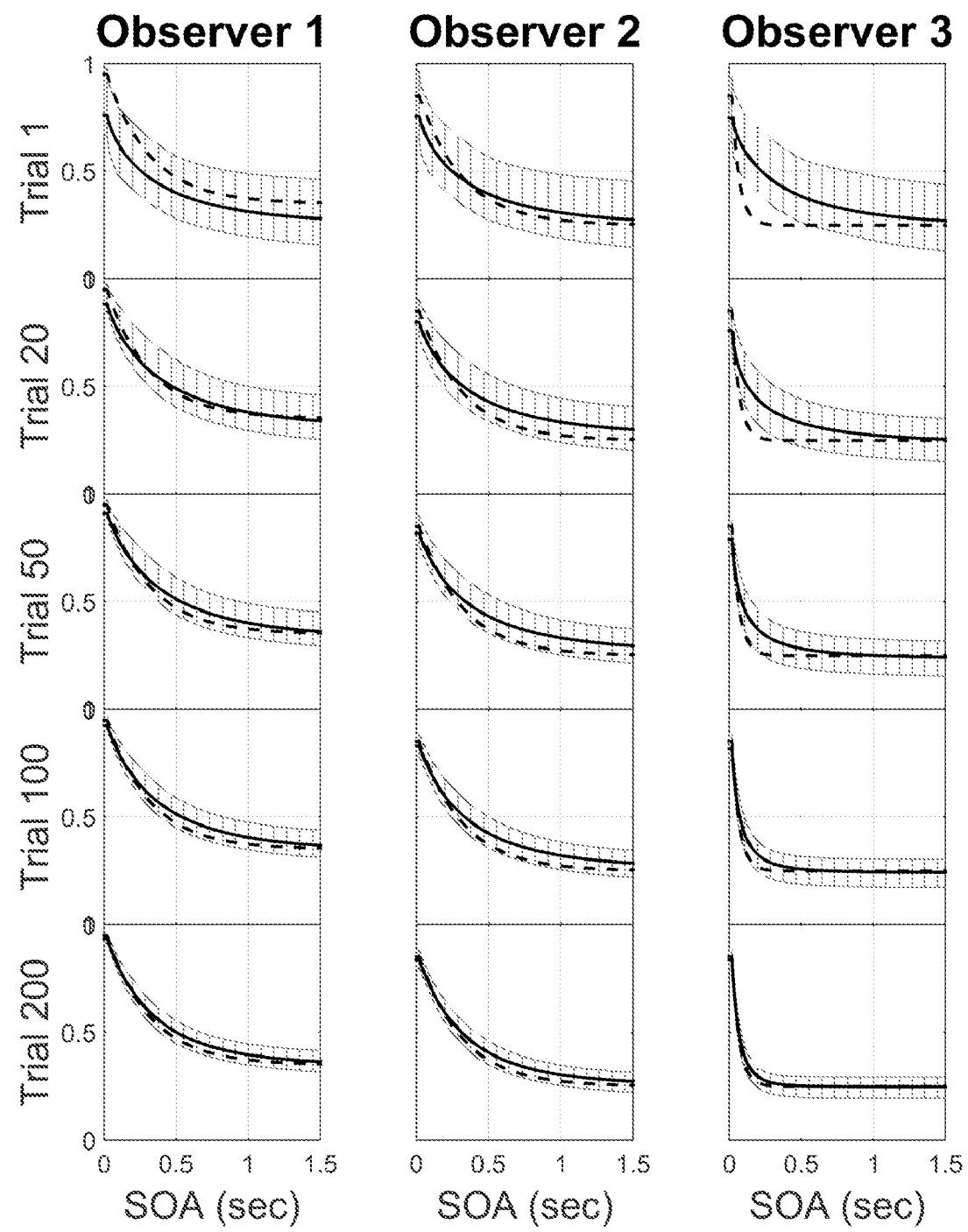
FIG. 8 shows the accuracy and precision of the iconic memory decay functions obtained with 25, 50, 100, and 200 adaptive PR trials.

FIG. 8 shows the accuracy and precision of the iconic memory decay functions obtained with 25, 50, 100, and 200 adaptive PR trials. Results of three observers are presented in different columns. The true decay functions are plotted as dashed curves, and the adaptive PR estimates are shown as black curves. Shaded areas represent 67% credible interval of adaptive PR estimates. With increasing trial numbers, adaptive PR improves accuracy (decreasing discrepancy between dashed and black curves) and precision (decreasing shaded area). As trial number increases (50-200 trials), the discrepancy between the true and estimated decay functions decreases. It takes less than 20 trials to recover the general shape of the true decay function for simulated observer 1 and 2, but 80 trials for observer 3 (|bias|<2.5%). This is because the decay time constant of observer 3 is near the edge of the uniform prior used in the simulation. The shaded region represents the average 67% credible interval. It becomes smaller than 10% after 33 trials for all observers, and afterward drops to below 7.5% after 80 trials and 5% after 200 trials. Bias and precision after 20, 50, 100, and 200 trials are summarized in Table 2 of FIG. 9. The results indicate that adaptive PR rapidly estimates the true iconic memory decay function for all potential populations with only a small number of trials.

Figure 11:
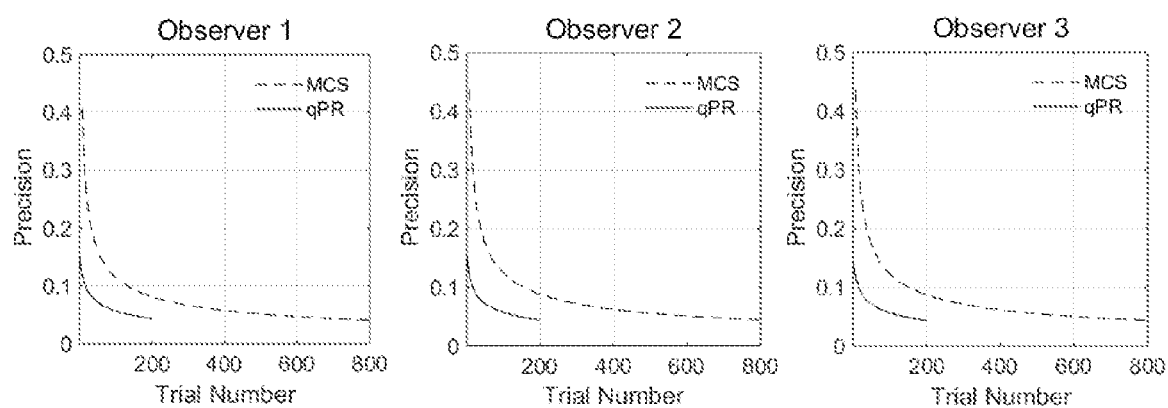
FIG. 11 provides graphs comparing the precision of the adaptive PR and MCS procedures for three observers.

To directly compare the efficiency of MCS and adaptive PR, one can compute the expected standard deviation of MCS procedure as a function of test trials by:

$$SD_i^{MCS} = \frac{\sum_i \sqrt{\frac{pc_i(1-pc_i)}{n_i}}}{I} \quad \text{(eq. 4)}$$

where $pc_i$ is the true percent correct at the i-th SOA, $n_i$ is the number of trials tested at the i-th SOA. Here it is assumed that eight SOA were tested in the MCS method (I=8) so that the number of tested trials is $n_i \times 8$. A comparison between the standard deviation of the MCS and the width of the average 67% credible interval of the adaptive PR procedure is presented in Table 3 (FIG. 10) and FIG. 11. The comparison was made between the standard deviation of MCS (blue) and the half width of the average 67% credible interval in the adaptive PR procedure (red). To reach a 7.5% precision, the MCS requires 240-270 trials, while the adaptive PR only needs 40-80 trials. To reach a 5% precision, the MCS requires 540-620 trials, while the adaptive PR only needs 140-190 trials. In sum, the adaptive PR is 3-5 times more efficient than the MCS. In terms of testing time, using the adaptive PR, an iconic memory decay function can be estimated with reasonable accuracy and precision in less than 10 minutes, which is considerably faster than the one hour of testing time with the conventional MCS.

Figure 12:
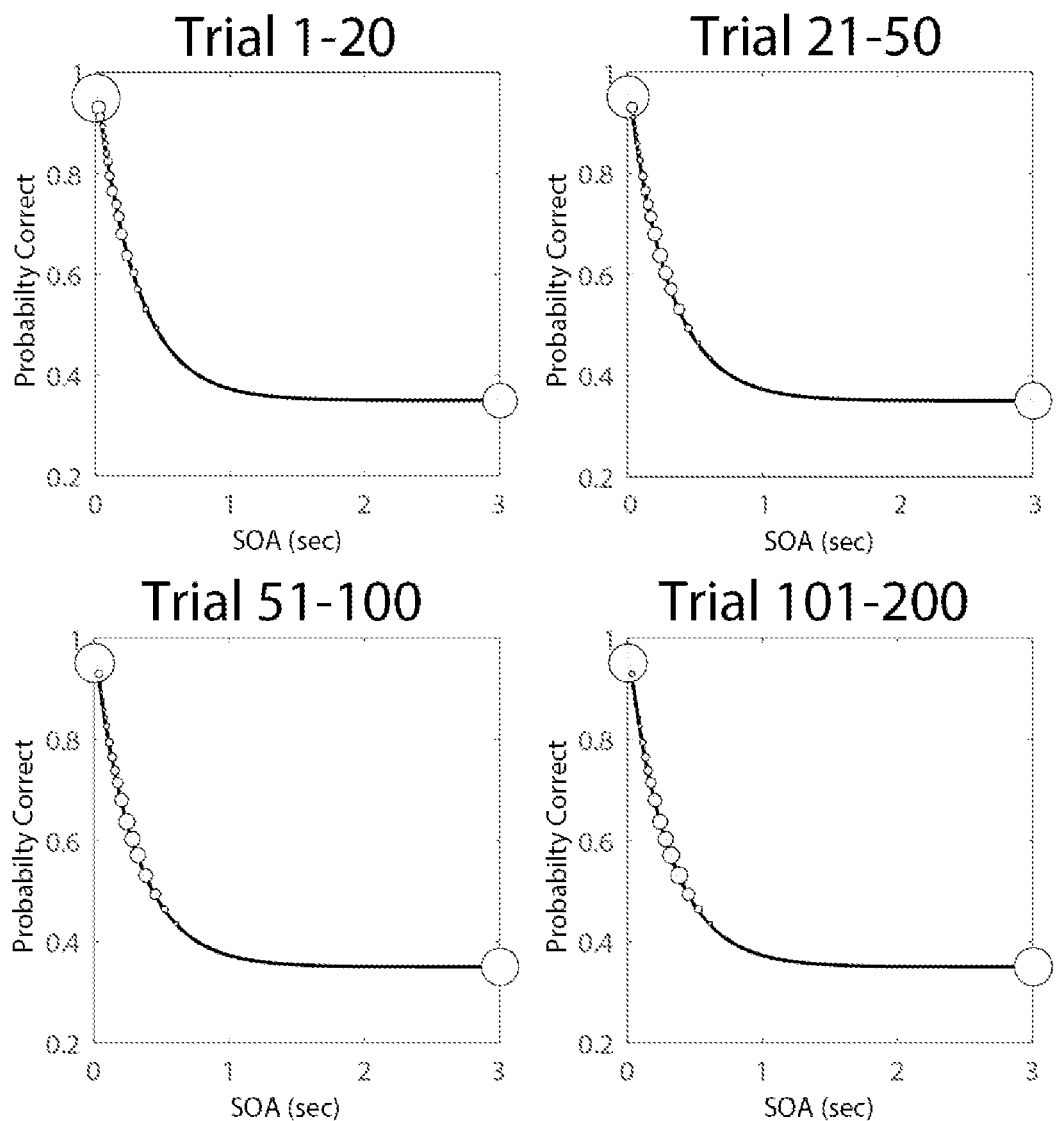
FIG. 12 provides graphs of stimulus sampling for observer 1.

Stimulus sampling by the adaptive PR procedure for observer 1 is presented in FIG. 12. The relative frequency of tested trials is presented as a function of SOA, overlaid on the true decay function. The size of the circles represents the proportion of tested trials in trials 1-20, 21-50, 50-100, and 101-200 trials in each SOA condition over 300 simulations. At the beginning, sampling is focused on the shortest (0 sec)

and longest (3 sec) SOAs to specify $a_0$ and $a_1$. Then it spreads to small SOAs (0-0.3 sec) and moved to the true $\tau$ value (0.3 sec). The size of the circles in each panel represents the proportion of tested trial as a function of SOA in trials 1-20, 21-50, 51-100, and 101-200. In the first 20 trials, the adaptive PR intensively tests the shortest and longest SOAs to characterize $a_0$ and $a_1$, with only a few trials on small SOAs (0-0.3 sec). Then the stimulus sampling of adaptive PR spreads to small SOAs and progressively moves to the range around the true $\tau$ value (0.2-0.4 sec). The method does not frequently tested SOAs greater than 0.5 sec (except 3 sec) throughout the whole experiment.

Figure 13:
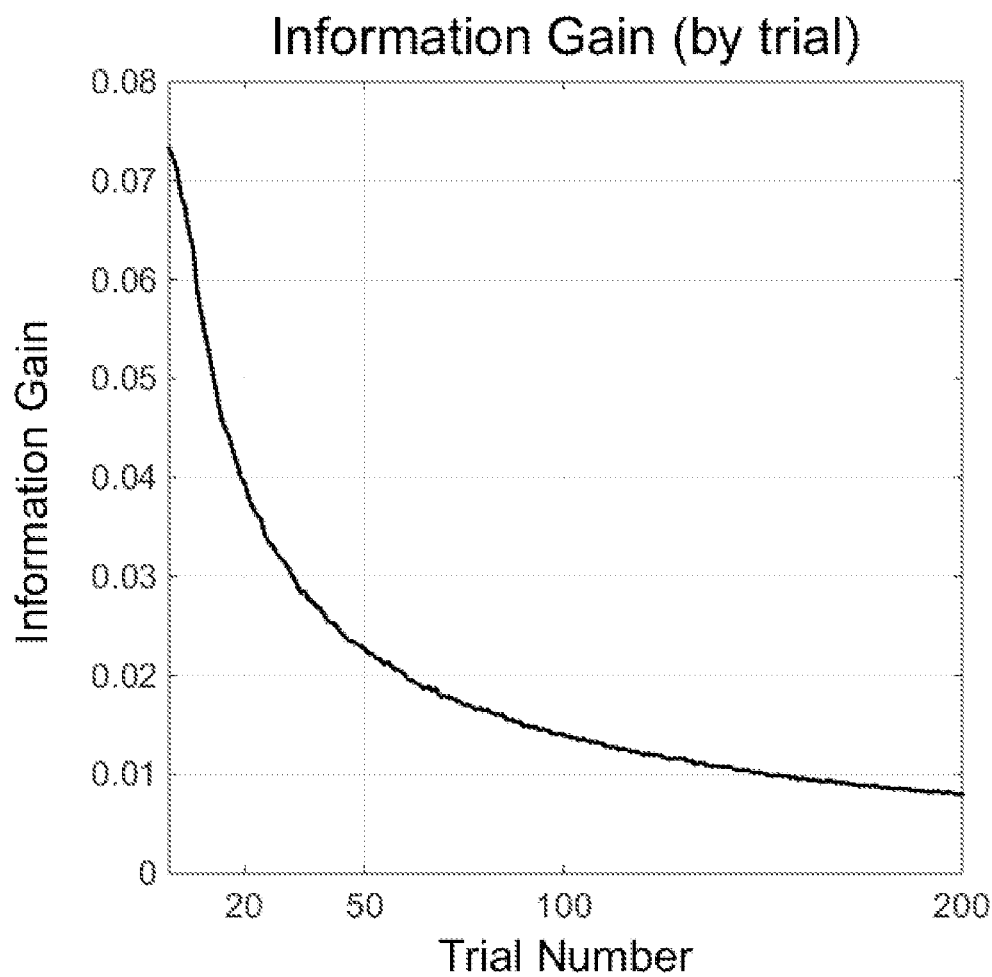
FIG. 13 is a graph representing information gain for simulated Observer 1.

FIG. 13 shows the amount of information obtained by using adaptive stimulus selection to test the optimal stimulus on each trial. The expected information gain is presented as a function of trial number. It is evident that the adaptive PR maximizes information gain so that the earlier trials provide much more information than later trials. In simulations of observer 1, for instance, the information gain of the first trial is 5 times more than the 100th trial, and 9 times more than the 200th trial.

Figure 14:
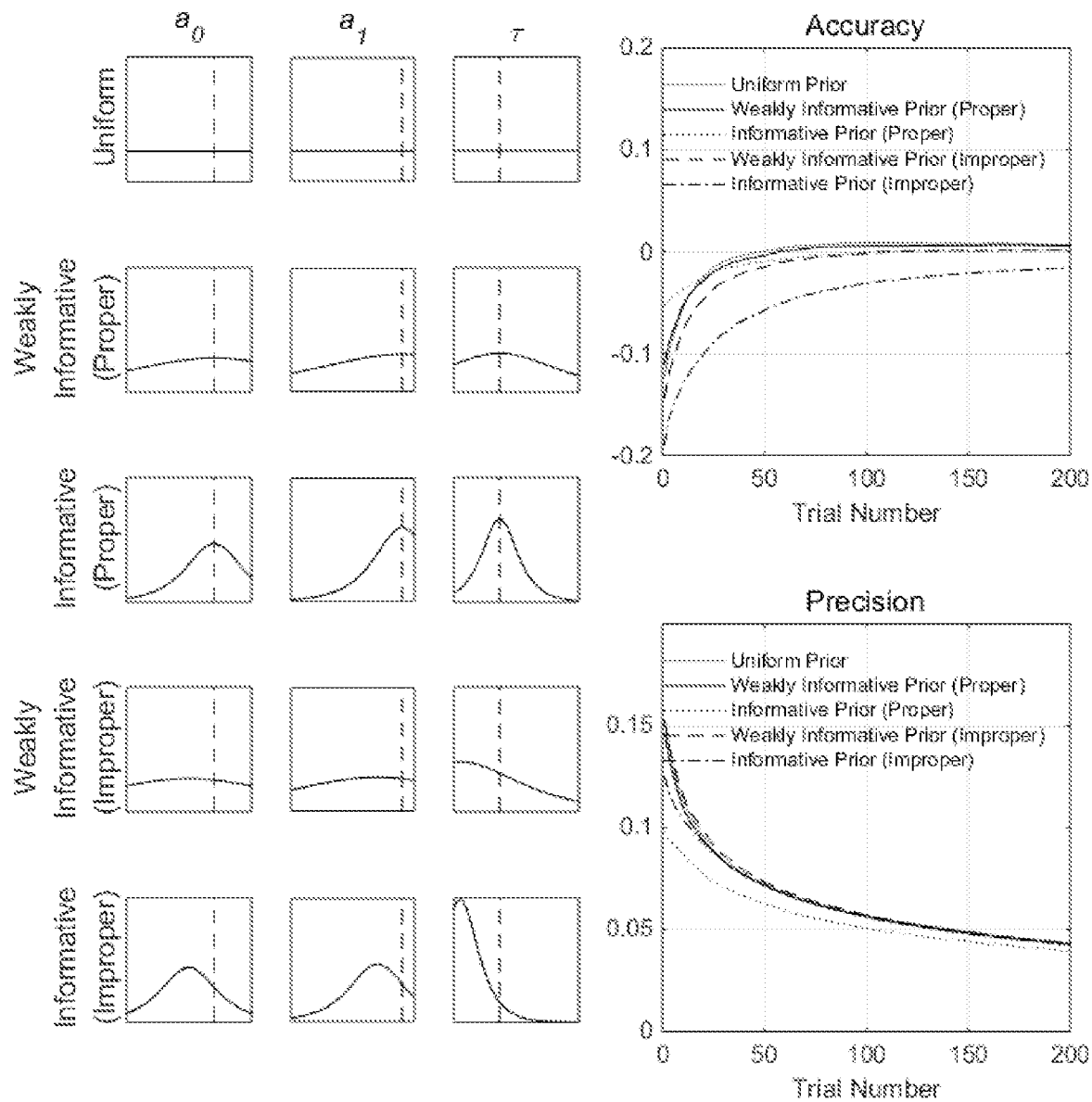
FIG. 14 includes graphs representing effects of the prior for observer 1.

In these simulations, the prior probability distribution was set to a uniform distribution over each dimension of the parameter space. Alternatively, it is possible to use prior knowledge to focus more narrowly on likely values of the parameters. Using a different setting for the initial prior distribution would change the starting point of parameter estimation and make the estimation process even faster and more efficient. To illustrate the effects of the prior, another set of simulation was conducted with five different prior settings: (1) a uniform prior distribution, (2) a weakly informative proper prior, (3) a weakly informative improper prior, (4) an informative proper prior, and (5) an informative improper prior. FIG. 14 represents effects of the prior for observer 1. Figures in the left panel show initial priors of the three parameters in the five different settings. The performance of the adaptive PR is shown in the right panels. FIG. 14 shows that the adaptive PR with a weakly informative priors—either proper or improper—has essentially the same performance as the one with a uniform prior after 30 trials and that an informative proper prior can enhance the performance of the procedure, but there is a risk of getting deteriorated accuracy when the informative prior is improper. In practice, the prior for the adaptive PR procedure can be informed by prior knowledge or pilot data, such as the representative parameter distribution of a known population obtained before testing a particular individual of that population.

Figure 15:
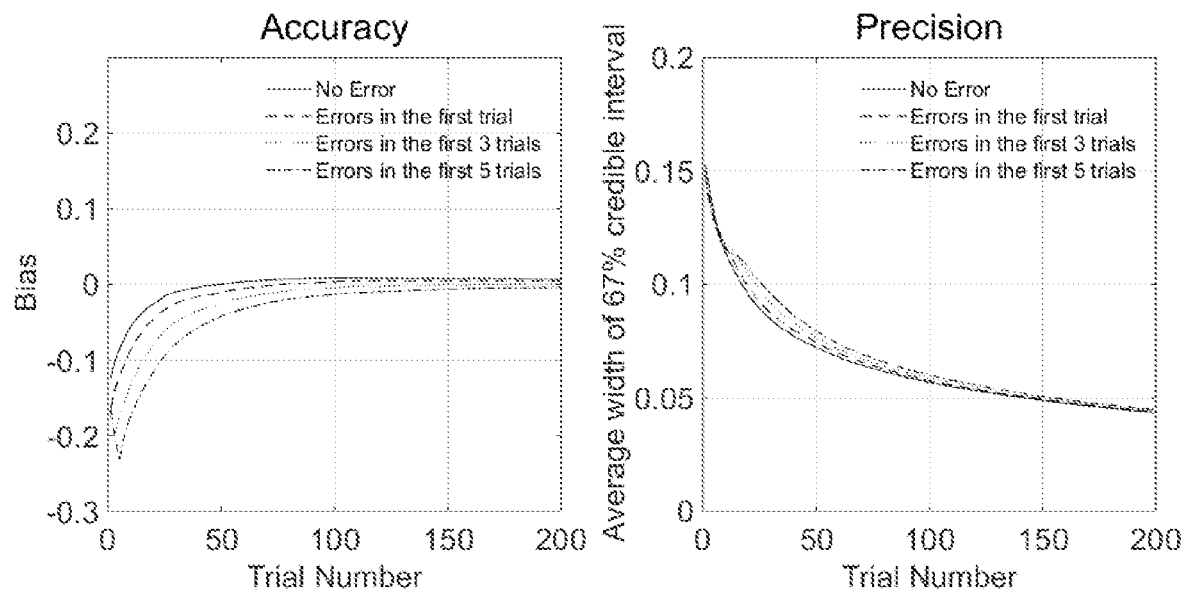
FIG. 15 is a graph representing effects of lapse in the first few trials.

One common problem in Bayesian adaptive procedures is that they are often vulnerable to mistakes (e.g., finger errors) made at the beginning of an experiment. Because adaptive PR obtains much more information in earlier trials than later trials, mistakes in the first few trials might cause inaccurate and imprecise estimation. To investigate the effect of lapse, observer 1 was simulated with random responses in the first 1, 3, and 5 trials, that is, the expected probability correct was at the chance performance level for all SOAs in the lapse trials. FIG. 15 shows that a small number of lapse trials in the beginning of the experiment does not have much impact on precision, but significantly slows down accurate estimation. To reach a less than 2.5% bias, for example, 20, 30, 50, and 70 trials are required in the simulation with lapse in the first 0, 1, 3, and 5 trials, respectively. However, adaptive PR recovers from observer's initial lapse and obtains sufficiently accurate estimation (bias<1.0%) after 80-120 trials in all the simulated conditions.

Responses due to lapse can be identified by the experimenter/clinician or a computer algorithm that simulates the experimenter. Such trials can be either repeated or eliminated from the procedure. The computer algorithm monitors the observer's response in each trial. Based on known characteristics of the observer and the current estimate of the observer's expected performance level, the algorithm determines the likelihood that the observer is in lapse and prescribes a remedy (e.g., a re-run of the trial condition).

Figure 16:
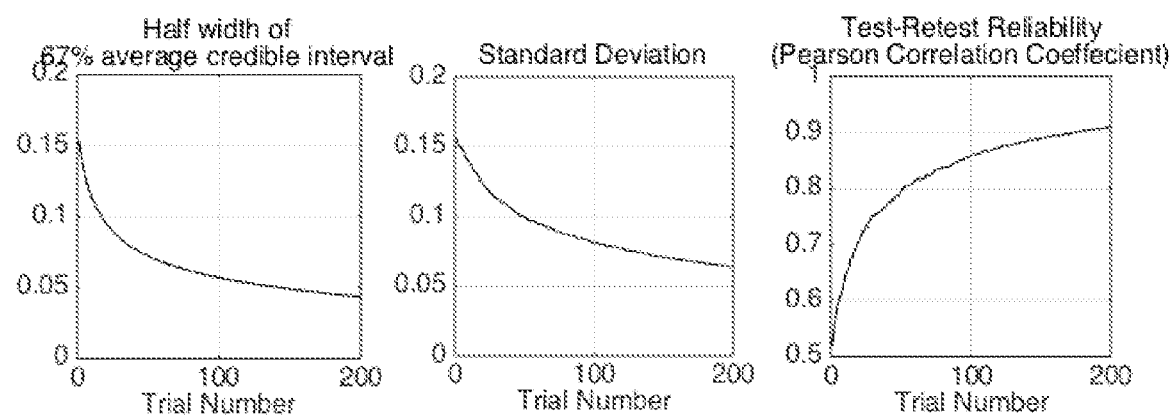
FIG. 16 are graphs representing precision and test-retest reliability of observer 1.

Different indices of precision in the simulated observer 1, the half width of average 67% credible interval and standard deviation, have been compared. FIG. 16 shows that both indices decreased with trial number. Both are starting at 0.16, but the credible interval showed slightly faster convergence. As the credible interval becomes smaller, test-retest reliability also increases.

Figure 17:
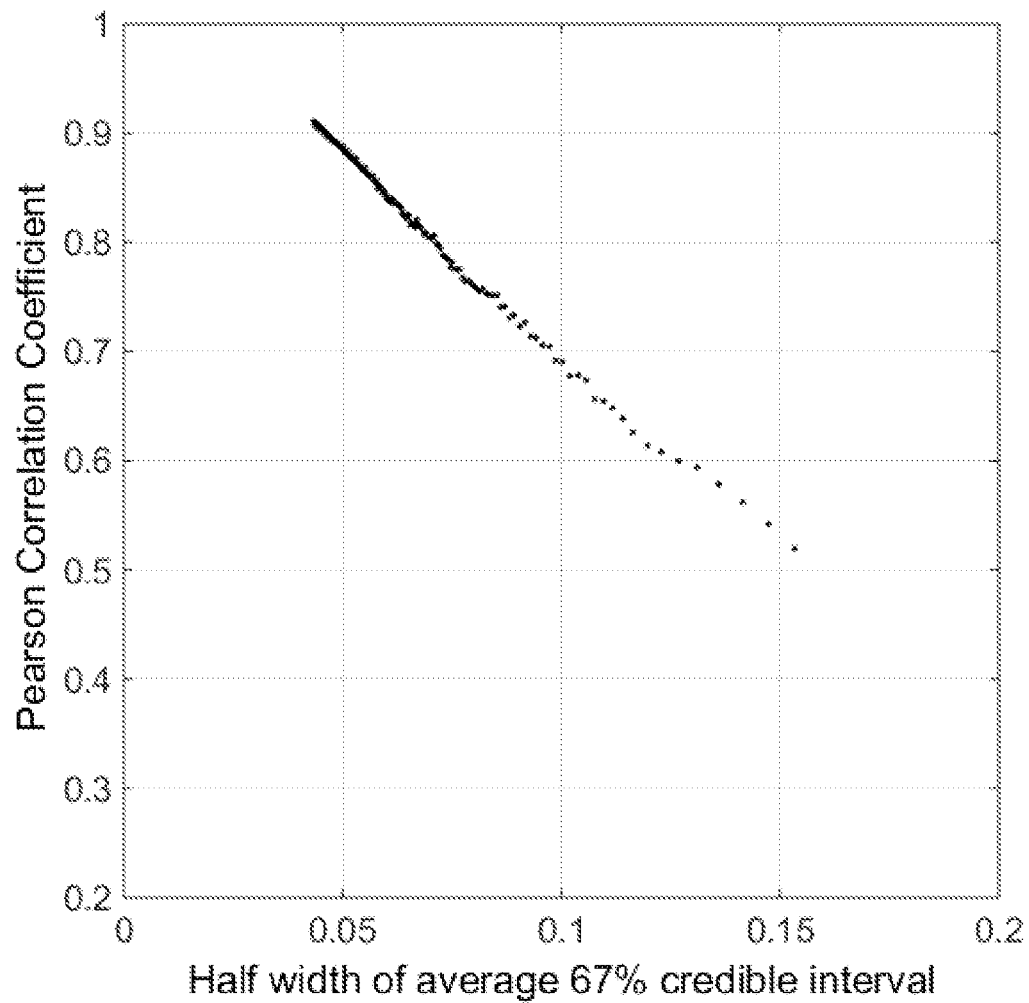
FIG. 17 is graph providing a relationship between credible interval and test-retest reliability (Simulated Observer 1).

The relationship between credible interval and test-retest reliability was also investigated. Pearson correlation coefficient increased as trial number increased, and achieved 0.9 at 200th trial. FIG. 17 provides a relationship between credible interval and test-retest reliability (simulated observer 1). The half width of average credible interval is negatively correlated with test-retest reliability.

In addition to the simulation study, the performance of adaptive PR method was validated with a psychophysical experiment. The iconic decay functions estimated by 100 adaptive PR trials had good precision and excellent agreement with those obtained with 1600 MCS trials.

Three observers (FH, TC, and JB) participated in the experiment. All observers were males between ages 34 and 44 years and had corrected-to-normal vision. They were experienced in psychophysical studies.

The experiment was carried out on an IBM PC compatible computer, running Psychtoolbox extensions (which can be found at http://psychtoolbox.org/, for example). The stimuli were displayed on a Dell 17-inch color CRT monitor, whose refresh rate was set at 100 Hz. Stimuli were viewed binocularly with natural pupil at a viewing distance of approximately 85 cm in a dimly lighted room.

Eight adaptive PR and one MCS measures were collected for each observer in four testing sessions. Each session consisted of 400 adaptive PR trials and 400 MCS trials: two interleaved adaptive PR runs with 200 trials each, and 50 MCS trials at each of eight SOA conditions. All trials were randomly mixed in each session.

A fixation cross was presented in the center of the display and remained until the end of each trial. The stimulus display, containing ten letters, appeared for 20 ms. The letters were ["C", "D", "H", "K", "N", "O", "R", "S", "V", "Z"], and equally spaced, in a random order, on an imaginary circle with an eccentricity of 3.5° from the central fixation. Each letter subtended a visual angle of 1.25°×1.25° and was drawn in capital Sloan optotype to control perceptual legibility. The letters were followed by a central cue pointing to one of the letters, with a selected SOA. For MCS trials, eight SOAs were used: the arrow cue was presented 0, 0.03, 0.06, 0.14, 0.30, 0.65, 1.4, or 3 sec after the onset of the letter display. For adaptive PR trials, the procedure selected SOAs among the 30 possible SOAs between 0 and 3 sec with log-linear spacing. The cue remained on until response. Observers were asked to report the cued letter with a standard keyboard, and a beep followed each incorrect response. An example of the trial sequence is illustrated in FIG. 1a. Each session took approximately one hour, with a short break after every 200 trials.

Figure 18:
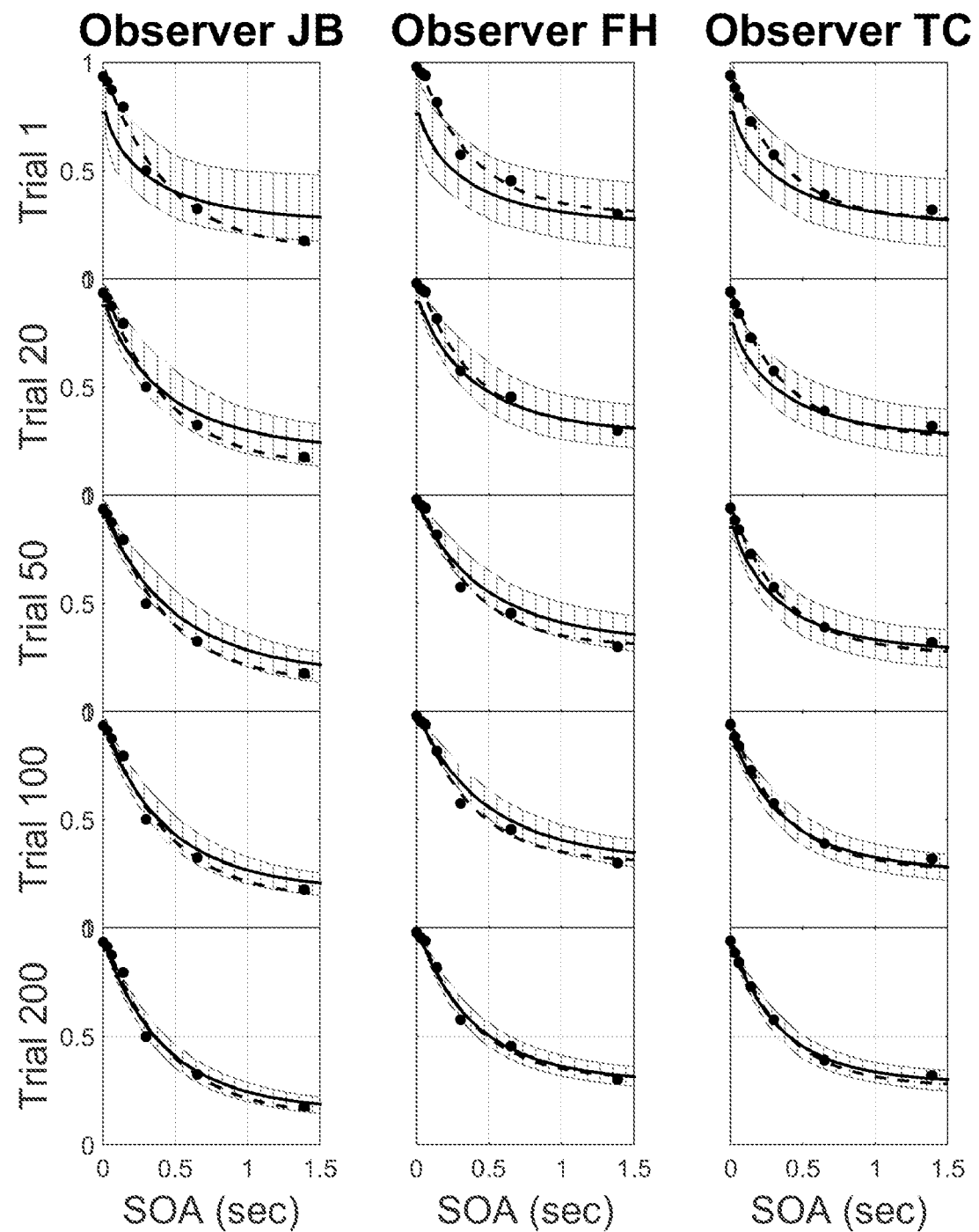
FIG. 18 graphs representing results from the psychophysical experiment for three observers.
Figures 19, 20:
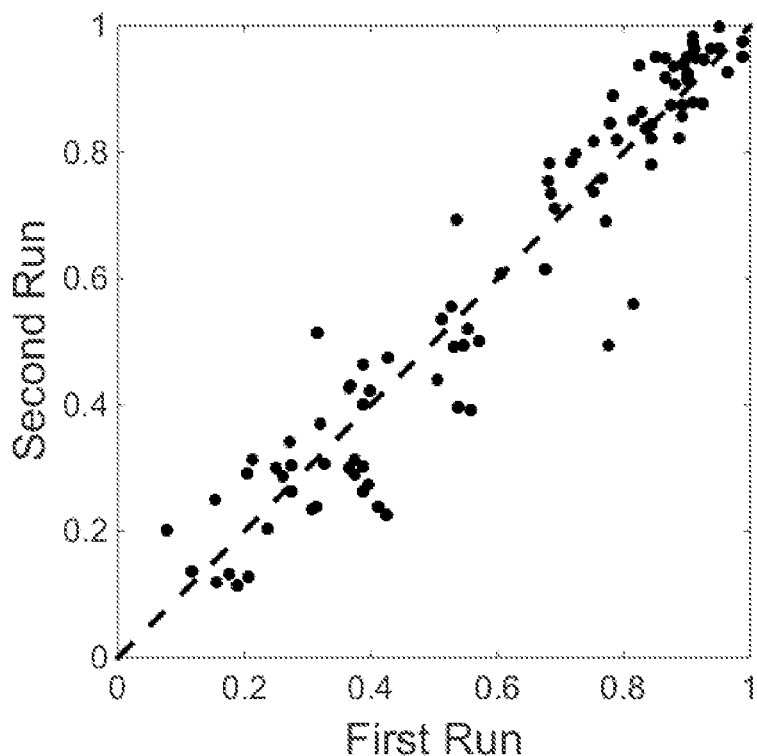
FIG. 19 is a table providing accuracy and precision of adaptive PR in a psychophysical experiment.
FIG. 20 is a graph representing a test-retest reliability for the two adaptive PR runs in each session (after 200 trials).

FIG. 18 presents each observer's decay functions measured with two methods: eight adaptive PR estimates (lines)

and MCS obtained with 1600 trials (circles). The data from the MCS method was fitted using Eq. 1 with a maximum likelihood procedure. The error region (shaded area) represents the mean width of 67% credible intervals from eight adaptive PR runs. Each column presents data from a different observer, and each row presents adaptive PR estimates obtained with different number of adaptive PR trials: 20, 50, 100, and 200. Agreement of the two methods and the precision of the adaptive PR estimate with the corresponding number of trials are summarized in Table 4 (FIG. 19).

FIG. 18 shows that the iconic memory decay functions obtained with the two methods overlapped with each other. Bias is evaluated by the root mean squared error (RMSE) between the estimated percent correct from the adaptive PR procedure and the MCS procedure at the eight SOAs common to both methods:

$$RMSE = \sqrt{\frac{\sum_k \sum_j \sum_i (pc_{ijk}^{qPR} - pc_{ijk}^{MSC})^2}{I \times J \times K - 1}} \quad \text{(eq. 5)}$$

where $pc_{ijk}^{qPR}$ and $pc_{ijk}^{MCS}$ are the estimated percent correct at i-th SOA of j-th run in k-th observer by the two methods. RMSE, starting with 14.9% at the first trial and reaching 4.9% after 200 adaptive PR trials.

The precision of the adaptive PR procedure is illustrated by the credible interval as a function of trial number in FIG. 18. For each observer, the average 67% credible interval for each SOA is obtained with 20, 50, 100 and 200 adaptive PR trials. Results clearly show that the credible interval of the estimated iconic memory decay functions decreases with increasing trial number (e.g., 3.9% after 200 adaptive PR trials).

Test-retest reliability is also assessed with analysis of the two adaptive PR runs in each session. FIG. 20 shows probability correct (at 8 SOAs×4 sessions×3 observers) estimated from the second adaptive PR runs against those from the first runs. Pearson's correlation coefficient was 0.9582 after 200 trials (p<0.001). The Pearson correlation coefficient is 0.98, across all testing sessions.

Therefore, an adaptive partial report procedure was developed based on a Bayesian adaptive framework to directly estimate the parameters of the sensory memory decay function with greatly reduced testing times. In adaptive PR, estimates of the parameters of the exponential decay function can be characterized by probability distributions. Starting with a prior distribution of the parameters, the adaptive PR method may select the most informative SOA, by evaluating the stimulus space to find the SOA stimulus condition that would provide the maximum expected information gain or minimum entropy. The methods can then update the probability distribution of the parameters based on the observer's response by Bayesian inference. The procedure is iterated until either the total number of trials reaches a set value or the precision of the parameter estimates reaches a certain criterion.

Compared to the conventional MCS procedure, the adaptive PR uses a much broader range and finer resolution of stimulus sampling space. The adaptive PR estimates the whole shape of iconic memory function with much less testing, since it concurrently measures performances across all different SOAs and utilizes all available information acquired during the experiment as well as prior knowledge about the mathematical form of the iconic memory decay function.

Results from simulations and the psychophysical experiment showed that the adaptive PR method requires only 100 trials of data collection to measure the sensory memory decay function with reasonable accuracy and precision. Simulation studies suggest that only 100 trials are necessary to reach a ±2.5% accuracy and a 7.5% precision. The method was also validated in a psychophysical experiment. Estimates of the sensory memory decay function obtained with 100 adaptive PR trials showed good precision (the half width of average 67% credible interval=5.1% pc) and excellent agreement with those obtained with 1600 trials using the conventional procedure (mean RMSE=5.7%). With the adaptive PR procedure, reasonably precise estimates can be obtained in 5-10 mins, which is significantly less than one hour required of conventional laboratory measurements.

The prior in the adaptive PR procedure can be informed by knowledge about the parameters of the iconic memory decay function as a function of the task, stimulus or test population. A proper informative prior can further speed up the estimation process. Often researchers use a broadly spread bell-shape distribution centered on the most probable value (e.g. Gaussian or hyperbolic secant distribution) to gain some benefit of prior knowledge but at the same time avoid some of the risk from using an inadequate prior. Alternatively, the prior could be a uniform distribution over the entire parameter space, when researchers do not have much prior knowledge of the parameters of the iconic memory decay function. In our psychophysical experiment, we used a uniform prior distribution for each adaptive PR parameter. A weakly informative prior based on prior knowledge of the parameters would make the measurement even more efficient, when a researcher wants to run an experiment with a relatively homogeneous observer population.

The adaptive PR procedure, like most other adaptive procedures, is vulnerable to lapses at the beginning of experiments, since the methods acquire much more information than later trials. In addition, although 'one-step ahead search'—finding the 'current best' stimulus for the next trial—has been proved to be efficient in many adaptive procedures, the greedy search algorithm is not necessarily the optimal strategy over the course of the whole experiment. Efficiency and robustness of methods could be improved by adopting global optimization or 'multiple-step ahead strategy'.

The adaptive PR procedure herein assume a single functional form, but sometimes there could be two or more competitive models that could describe data well (e.g. exponential function vs. power function for the temporal property of memory decay). It would be useful to combine selecting the best model among several different models with estimating parameters of each model into a single procedure.

Hierarchical Bayesian modeling could provide even greater efficiency by better-informed priors across sessions or observers based on statistical dependency of data.

In one detailed method, before the procedure, define (1) a three dimensional $(a_0, a_1, \tau)$ parameter space, $\vec{v}$, that represents many possible empirical sensory memory decay functions, (2) the one-dimensional stimulus search space, $\vec{x}$, over the possible levels of stimulus intensity, SOA, and (3) a prior probability density function $p_t(\vec{v})$, that represents a priori knowledge of the observer's sensory memory decay functions. The partial report function is modeled with exponential decay functions:

$$p(\text{correct}, \vec{x} \mid \vec{v}) = a_0 + (a_1 - a_0)e^{-x/\tau}$$

$$p(\text{incorrect}, \vec{x} | \vec{v}) = 1 - [a_0 + (a_1 - a_0)e^{-x/\tau}] \quad \text{(eq. 6)}$$

During the experiment, Bayesian inference is used to update the joint probability density function, and its corresponding parameter estimates. The probability of a correct response given stimulus is estimated by weighing empirical response rates by the prior:

$$p(\text{correct}/\vec{x}) = \sum_{\vec{v}} [p(\text{correct}, \vec{x}) \times p(\vec{v})] \quad \text{(eq. 7)}$$

The posterior probability distribution $p_{t+1}(\vec{v})$ following a correct and an incorrect response to each possible stimulus $\vec{x}$ in the next trial (trial t+1) is:

$$p_{t+1}(\vec{v}/\vec{x}, \text{correct}) = \frac{p(\text{correct}/\vec{x}, \vec{v})}{\sum_{\vec{v}} [p_t(\vec{v}) \times p(\text{correct}/\vec{x}, \vec{v})]} \times p_t(\vec{v}) \quad \text{(eq. 8)}$$

$$p_{t+1}(\vec{v}/\vec{x}, \text{incorrect}) = \frac{p(\text{incorrect}/\vec{x}, \vec{v})}{\sum_{\vec{v}} [p_t(\vec{v}) \times p(\text{incorrect}/\vec{x}, \vec{v})]} \times p_t(\vec{v})$$

The posterior probability function is used as the prior probability function in the subsequent trial.

To obtain the most information about the observer's sensory memory decay function, the method selects the stimulus that minimizes the expected entropy for the posterior following the next trial. For each possible stimulus, the entropies of the simulated posteriors following a correct and an incorrect response are calculated:

$$H_{t+1}(\vec{x}, \text{correct}) = \quad \text{(eq. 9)}$$
$$-\sum_{\vec{v}} [p_{t+1}(\vec{v}/\vec{x}, \text{correct}) \times \log(p_{t+1}(\vec{v}/\vec{x}, \text{correct}))]$$

$$H_{t+1}(\vec{x}, \text{incorrect}) =$$
$$-\sum_{\vec{v}} [p_{t+1}(\vec{v}/\vec{x}, \text{incorrect}) \times \log(p_{t+1}(\vec{v}/\vec{x}, \text{incorrect}))]$$

The expected entropy after trial with stimulus $\vec{x}$ is then calculated by weighing posterior entropies by response probabilities:

$$E[H_{t+1}(\vec{x})] = H_{t+1}(\vec{x}, \text{correct}) \times p_{t+1}(\text{correct}|\vec{x}) + H_{t+1}(\vec{x}, \text{incorrect}) \times p_{t+1}(\text{incorrect}|\vec{x}) \quad \text{(eq. 10)}$$

In the next trial (trial t+1), the stimulus with the minimum expected entropy is presented:

$$\vec{x}_{t+1} = \underset{\vec{x}}{\arg\min} E[H_{t+1}(\vec{x})] \quad \text{(eq. 11)}$$

The method terminates either when the total number of trials reaches a pre-specified value (as implemented in this paper) or when the precision of the threshold estimate reaches a pre-determined level.

Thus, the invention provides, among other things, an adaptive method that efficiently provides estimates of the sensory memory decay function. Various features and advantages of the invention are set forth in the following claims.

What is claimed is:

1. A method of generating an adaptive partial report (adaptive PR) for an observer with an apparatus comprising a display, a user interface, and a processor, the method comprising
the processor characterizing an iconic memory decay function for the observer, the iconic memory decay function having a plurality of parameters, the characterization including determining a prior for the plurality of parameters;
the processor determining a first stimulus for a first trial based on the prior of the parameters, the determined first stimulus being expected to lead to an information gain for the iconic memory decay function;
the display generating the first stimulus for viewing by the observer;
the user interface receiving input for the first trial and in response to the first stimulus;
the processor revising a posterior distribution of parameter values for the parameters based on the received input;
the processor determining a new stimulus for a next trial based on the revised posterior distribution, the determined new stimulus being expected to lead to additional information gain for the iconic memory decay function;
the display generating the new stimulus for viewing by the observer;
the user interface receiving new input for the next trial and in response to the new stimulus; and
the processor revising the posterior distribution of the parameter values for the parameters based on the new input,
wherein the iconic memory decay function takes the form of $$pc(SOA) = a_0 + (a_1 - a_0)e^{-SOA/\tau}$$

where pc(SOA) is the probability of making a correct response at cue delay time SOA, $a_0$ is the asymptotic performance level, $a_1$ is the performance level when SOA=0, and $\tau$ is the time constant of memory decay—the time it takes for performance to drop to 37% of its initial level.

2. The method of claim 1, wherein the prior provides a broad distribution for the parameters $a_0$, $a_1$, and $\tau$.

3. The method of claim 1, wherein the processor revises the posterior distribution of the parameter values for the parameters based on the new input by Bayesian inference.

4. The method of claim 1, further comprising repeating the steps of determining a new stimulus, generating the new stimulus, receiving new input, and the revising posterior distribution of parameter values for the parameters based on the new input until a stop rule is reached.

5. The method of claim 4, wherein the stop rule is based on a level of precision for a defined objective.

6. The method of claim 5, wherein the defined objective includes a credible interval of the iconic memory decay function.

7. The method of claim 5, wherein the defined objective includes a single decay time constant.

8. The method of claim 1, wherein the revised posterior distribution of parameter values for the parameters based on the new input maximizes an expected information gain of the iconic memory decay function.

9. The method of claim 8, determining a value for SOA to maximize the expected information gain of the iconic memory decay function.

10. The method of claim 1, wherein the revised posterior distribution of parameter values minimize at least one of credible intervals of single partial report parameters, credible regions of the estimated partial report functions, and uncertainty of class membership in patient discrimination.

11. The method of claim 1, wherein the revised posterior distribution of parameter values maximize at least one of a probability gain for a hypothesis of class membership, and an expected change in Kullback-Leibler distance between a Bayesian prior and posterior.

12. A method of generating an adaptive partial report (adaptive PR) for an observer with an apparatus comprising a display, a user interface, and a processor, the method comprising
   the processor characterizing an iconic memory decay function for the observer, the iconic memory decay function having a plurality of parameters, the characterization including determining a prior for the plurality of parameters;
   the processor determining a first stimulus for a first trial based on the prior of the parameters, the determined first stimulus being expected to lead to an information gain for the iconic memory decay function;
   the display generating the first stimulus for viewing by the observer;
   the user interface receiving input for the first trial and in response to the first stimulus;
   the processor revising a posterior distribution of parameter values for the parameters based on the received input;
   the processor determining a new stimulus for a next trial based on the revised posterior distribution, the determined new stimulus being expected to lead to additional information gain for the iconic memory decay function;
   the display generating the new stimulus for viewing by the observer;
   the user interface receiving new input for the next trial and in response to the new stimulus; and
   the processor revising the posterior distribution of the parameter values for the parameters based on the new input, wherein the processor revises the posterior distribution of the parameter values for the parameters based on the new input by Bayesian inference,
   wherein the Bayesian inference follow Bayes rule $$p_t(\vec{v} \mid r_t) = \frac{p(r_t \mid \vec{v})}{\sum [p_t(\vec{v}) \times p(r_t \mid \vec{v})]} \times p_t(\vec{v})$$

where $\vec{v}=(a_0, a_1, \tau)$ represents parameters of the sensory memory decay function, $p_t(\vec{v})$ is the prior probability density function of $\vec{v}$, $p_t(r_t/\vec{v})$ is the likelihood of observing a response (correct or incorrect) given $\vec{v}$, $r_t$ is observer's response in trial t, $p_t(\vec{v}|r_t)$ is the posterior distribution of $\vec{v}$ after the t-th trial.

13. The method of claim 12, wherein the iconic memory decay function includes an exponential decay function having a first parameter representative of performance at long delays, a second parameter representative of performance at the simultaneous cue, and a third parameter representative of a time constant for the decay.

14. The method of claim 13, wherein the initial parameter values provide a broad prior distribution with the first, second, and third parameters.

15. The method of claim 12, wherein the prior of parameter values is determined based on demographic information of the observer.

16. The method of claim 12, and further comprising the processor monitoring an expected performance level of the new input to determine the likelihood that the observer is in lapse.

17. The method of claim 16, and further comprising the processor not revising the posterior distribution of parameter values when the observer is in lapse.

18. An apparatus for generating an adaptive partial report, the apparatus comprising:
   a display;
   a user interface
   a processor; and
   a non-transitory medium comprising instructions that when executed by the processor cause the processor to
      characterize an iconic memory decay function for an observer, the iconic memory decay function having a plurality of parameters, the characterization including determining a prior of parameter values for the plurality of parameters,
      determine a first stimulus for a first trial based on the prior of the parameters, the determined first stimulus being expected to lead to an information gain for the iconic memory decay function,
      cause the display to generate the first stimulus for viewing by the observer,
      receive from the user interface input for the first trial and in response to the first stimulus,
      revise posterior distribution of parameter values for the parameters based on the received input,
      determine a new stimulus for a next trial based on the revised parameter values, the determined new stimulus being expected to lead to additional information gain for the estimated iconic memory decay function,
      cause the display to generate the new stimulus for viewing by the observer,
      receive from the user interface new input for the next trial and in response to the new stimulus, and
      revise the posterior distribution of parameter values for the parameters based on the new input,
   wherein the non-transitory medium further comprises instructions that when executed by the processor cause the processor to
      revise the posterior distribution of the parameter values for the parameters based on the received input by Bayesian inference, and
      revise the posterior distribution of the parameter values for the parameters based on the new input by Bayesian inference,
   wherein the Bayesian inference follows Bayes rule $$p_t(\vec{v}/r_t) = \frac{p(r_t/\vec{v})}{\sum [p_t(\vec{v}) \times p(r_t/\vec{v})]} \times p_t(\vec{v})$$

where $\vec{v}=(a_0, a_1, \tau)$ represents parameters of the sensory memory decay function, $p_t(\vec{v})$ is the prior probability density function of $\vec{v}$, $p_t(r_t|\vec{v})$ is the likelihood of observing a response (correct or incorrect) given $\vec{v}$, $r_t$ is observer's response in trial t, $p_t(\vec{v}|r_t)$ is the posterior distribution of $\vec{v}$ after the t-th trial.

19. The apparatus of claim 18, wherein the non-transitory medium further comprises instructions that when executed by the processor cause the processor to repeat the acts of determining a new stimulus, generating the new stimulus, receiving new input, and the revising posterior distribution of parameter values for the parameters based on the new input until a stop rule is reached.

20. The apparatus of claim 18, wherein the revised posterior distribution of parameter values for the parameters based on the new input maximizes an expected information gain of the iconic memory decay function, wherein the non-transitory medium further comprises instructions that when executed by the processor cause the processor to determine a value for SOA to maximize the expected information gain of the iconic memory decay function.

\* \* \* \* \*

UNITED STATES PATENT AND TRADEMARK OFFICE
CERTIFICATE OF CORRECTION

PATENT NO. : 10,646,155 B2
APPLICATION NO. : 15/567028
DATED : May 12, 2020
INVENTOR(S) : Zhong-Lin Lu, Jongsoo Baek and Luis A. Lesmes Page 1 of 1

It is certified that error appears in the above-identified patent and that said Letters Patent is hereby corrected as shown below:

In the Specification

Column 1, Line 13, please insert the following paragraph:
-- STATEMENT OF GOVERNMENT INTEREST
This invention was made with government support under grant numbers R01 EY021553, EY017491, and MH081018 awarded by the National Institutes of Health. The government has certain rights in the invention. --

Signed and Sealed this
Eleventh Day of August, 2020

Andrei Iancu
*Director of the United States Patent and Trademark Office*